US012330314B2

(12) United States Patent
Gonenc et al.

(10) Patent No.: US 12,330,314 B2
(45) Date of Patent: Jun. 17, 2025

(54) SYSTEMS AND METHODS FOR DOCKING WITH A TROCAR

(71) Applicant: Verb Surgical Inc., Santa Clara, CA (US)

(72) Inventors: Berk Gonenc, Cupertino, CA (US); Xin Liu, Milpitas, CA (US); Jose Luis Cordoba, Malaga (ES); Bernhard A. Fuerst, Sunnyvale, CA (US); Dennis Moses, Hollywood, FL (US); Pablo Garcia Kilroy, Menlo Park, CA (US)

(73) Assignee: Verb Surgical Inc., Santa Clara, CA (US)

( * ) Notice: Subject to any disclaimer, the term of this patent is extended or adjusted under 35 U.S.C. 154(b) by 0 days.

(21) Appl. No.: 18/537,639

(22) Filed: Dec. 12, 2023

(65) Prior Publication Data

US 2024/0173865 A1 May 30, 2024

Related U.S. Application Data

(63) Continuation of application No. 18/063,940, filed on Dec. 9, 2022, now Pat. No. 11,911,910, which is a
(Continued)

(51) Int. Cl.
*B25J 9/16* (2006.01)
*A61B 17/34* (2006.01)
(Continued)

(52) U.S. Cl.
CPC ......... *B25J 9/1666* (2013.01); *A61B 17/3423* (2013.01); *A61B 34/32* (2016.02);
(Continued)

(58) Field of Classification Search
USPC .................................................. 700/245–264
See application file for complete search history.

(56) References Cited

U.S. PATENT DOCUMENTS

| | | | | |
|---|---|---|---|---|
| 8,527,033 B1 * | 9/2013 | Williams | .............. | A61M 5/427 600/424 |
| 11,529,734 B2 * | 12/2022 | Gonenc | .............. | A61B 17/3421 |

(Continued)

FOREIGN PATENT DOCUMENTS

| | | |
|---|---|---|
| JP | 2018-500054 A | 1/2018 |
| WO | 2018/217431 A1 | 11/2018 |

(Continued)

OTHER PUBLICATIONS

Gmerek, Artur, et al., "Admittance control of a 1-DoF robotic arm actuated by BLDC motor," 17th International Conference on Methods & Models in Automation & Robotics (MMAR), Aug. 27, 2012, 6 pages.

(Continued)

*Primary Examiner* — Jonathan L Sample
(74) *Attorney, Agent, or Firm* — Aikin & Gallant, LLP

(57) ABSTRACT

A surgical robotic system has a tool drive coupled to a distal end of a robotic arm that has a plurality of actuators. The tool drive has a docking interface to receive a trocar. The system also includes one or more sensors that are operable to visually sense a surface feature of the trocar. One or more processors determine a position and orientation of the trocar, based on the visually sensed surface feature. In response, the processor controls the actuators to orient the docking interface to the determined orientation of the trocar and to guide the robotic arm toward the determined position of the trocar. Other aspects are also described and claimed.

19 Claims, 13 Drawing Sheets

Related U.S. Application Data continuation of application No. 16/670,889, filed on Oct. 31, 2019, now Pat. No. 11,529,734.

(51) Int. Cl.

| | | |
|---|---|---|
| *A61B 34/32* | (2016.01) | |
| *A61B 34/35* | (2016.01) | |
| A61B 17/00 | (2006.01) | |
| A61B 34/10 | (2016.01) | |
| A61B 34/20 | (2016.01) | |
| A61B 90/50 | (2016.01) | |

(52) U.S. Cl.
CPC .............. *A61B 34/35* (2016.02); *B25J 9/16* (2013.01); *A61B 2017/00477* (2013.01); *A61B 2034/107* (2016.02); *A61B 2034/2055* (2016.02); *A61B 90/50* (2016.02)

(56) References Cited

U.S. PATENT DOCUMENTS

| | | | | |
|---|---|---|---|---|
| 11,911,910 | B2* | 2/2024 | Gonenc | A61B 34/37 |
| 2011/0046637 | A1* | 2/2011 | Patel | A61B 17/29 606/130 |
| 2011/0282351 | A1* | 11/2011 | Cooper | A61B 34/37 606/108 |
| 2013/0066335 | A1* | 3/2013 | Barwinkel | A61B 90/11 606/130 |
| 2015/0025549 | A1* | 1/2015 | Kilroy | A61B 90/361 606/130 |
| 2015/0359597 | A1* | 12/2015 | Gombert | B25J 9/0087 901/8 |
| 2016/0100898 | A1* | 4/2016 | Jinno | A61B 34/37 606/130 |
| 2016/0100899 | A1* | 4/2016 | Jinno | A61B 34/37 606/130 |
| 2017/0086930 | A1* | 3/2017 | Thompson | A61B 34/30 |
| 2017/0105811 | A1* | 4/2017 | Garbus | A61B 17/3476 |
| 2017/0238962 | A1* | 8/2017 | Hansen | A61B 90/37 |
| 2018/0078332 | A1* | 3/2018 | Mozes | A61C 3/02 |
| 2018/0168746 | A1* | 6/2018 | Swayze | A61B 17/3423 |
| 2019/0053824 | A1* | 2/2019 | Scheib | A61B 34/70 |
| 2019/0321115 | A1* | 10/2019 | Anderson | A61B 17/3423 |
| 2020/0268453 | A1* | 8/2020 | Fuerst | B25J 15/0019 |
| 2020/0405401 | A1* | 12/2020 | Shelton, IV | A61B 90/361 |
| 2020/0405403 | A1* | 12/2020 | Shelton, IV | A61B 17/3421 |
| 2020/0405406 | A1* | 12/2020 | Harris | A61B 46/40 |
| 2020/0405408 | A1* | 12/2020 | Shelton, IV | A61B 34/30 |
| 2023/0107870 | A1 | 4/2023 | Romo et al. | |

FOREIGN PATENT DOCUMENTS

| | | |
|---|---|---|
| WO | 2019/096933 A2 | 5/2019 |
| WO | 2019/096939 A1 | 5/2019 |
| WO | 2019/204699 A1 | 10/2019 |

OTHER PUBLICATIONS

He, Changyu, et al., "An Inertial and Optical Sensor Fusion Approach for Six Degree-of-Freedom Pose Estimation," Sensors, vol. 15, Jul. 8, 2015, pp. 16448-16465.

International Preliminary Report on Patentability for International Application No. PCT/US2019/059896 mailed May 12, 2022, 8 pages.

International Search Report and Written Opinion for International Application No. PCT/US2019/059896 mailed Jul. 23, 2020, 18 pages.

Notice of Allowance received for U.S. Appl. No. 18/063,940, mailed on Jan. 16, 2024, 7 pages.

Notice of Allowance received for U.S. Appl. No. 18/063,940, mailed on Jul. 26, 2023, 7 pages.

Notice of Allowance received for U.S. Appl. No. 18/063,940, mailed on Nov. 9, 2023, 10 pages.

Steidle, Florian, et al., "Optical-Intertial Tracking of an Input Device for Real-Time Robot Control," 2016 IEEE International Conference onRobtoics and Automations (ICRA), May 16, 2016, pp. 742-749.

Supplementary European Search Report and Search Opinion received for EP Application No. 19950240.2, mailed on Dec. 5, 2023, 16 pages.

Supplementary Partial European Search Report and Search Opinion received for EP Application No. 19950240.2, mailed on Oct. 18, 2023, 15 pages.

Unpublished U.S. Appl. No. 16/654,279, filed Oct. 16, 2019.

Office Action received for Japanese Patent Application No. 2022-525368, mailed on Mar. 5, 2024, 6 pages (3 pages of English Translation and 3 pages of Original Document).

Notice of Preliminary Rejection received for Korean Patent Application No. 10-2022-7018124, mailed on Jan. 24, 2025, 10 pages (7 pages of Original Document and 3 pages of English Translation).

* cited by examiner

SYSTEMS AND METHODS FOR DOCKING WITH A TROCAR

CROSS-REFERENCE TO RELATED APPLICATIONS

This application is a continuation of co-pending U.S. patent application Ser. No. 18/063,940, filed Dec. 9, 2022, which is a continuation of U.S. patent application Ser. No. 16/670,889, filed Oct. 31, 2019, now U.S. Pat. No. 11,529,734, issued Dec. 20, 2022, which are hereby incorporated by reference in their entirety.

TECHNICAL FIELD

This disclosure relates generally to the field of robotic surgery and, more particularly, to docking systems for surgical robotics or for use in robotic-assisted surgical systems where a surgical robotic arm needs to be docked with a trocar.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more tools and at least one endoscopic camera through the incisions into the patient. The surgical procedures are then performed by using the introduced tools, with the visualization aid provided by the camera. Generally, MIS provides multiple benefits, such as reduced patient scarring, less patient pain, shorter patient recovery periods, and lower medical treatment costs associated with patient recovery. In some embodiments, MIS may be performed with robotic systems that include one or more robotic arms for manipulating surgical instruments based on commands from an operator.

In MIS procedures, access is provided to the body cavity of a patient through a trocar. Once a distal end of a cannula of the trocar is properly positioned and inserted through tissue and into an interior region of the patient, for example, through the abdominal wall of the patient, a surgical robotic arm having a trocar docking interface at its distal end, or a tool drive attached thereto, is manually maneuvered by an operator until the docking interface is aligned with an attachment portion (e.g., a mating interface) on the proximal end of the trocar (outside the patient). The operator then latches the trocar mating and the trocar docking interfaces to each other, either manually or as an automated step, thereby rigidly attaching the arm to the trocar. Once docked in this manner, a surgical tool having an end effector at its distal end (e.g., scissors, grasping jaws, needle, energy emitter, or camera) is then inserted into a top opening of the cannula and the tool is then attached to the arm such that further surgical operations can be performed with the tool while remotely controlling the arm.

SUMMARY

In MIS procedures, once a cannula of a trocar is properly positioned and inserted through tissue and into an interior region of a patient, a robotic arm, or a tool drive attached thereto, needs to be docked to the trocar, to provide a rigid mechanical attachment of the robotic arm to the trocar. Such attachment of the robotic arm and the trocar to each other enables the robotic arm to move as one with the trocar and one or more surgical tools, where the latter have been inserted through a lumen of the cannula and into the interior region of the patient. A docking interface located on a distal block of the robotic arm, or on the tool drive that is attached to the arm, is maneuvered through control of actuators in the arm until the docking interface is aligned with and positioned at an attachment portion (e.g., a mating interface) of the trocar (that is exposed outside the patient). The docking interface of the robotic arm/tool drive is then latched to the attachment portion of the trocar, thereby providing a rigid mechanical attachment of the robotic arm/tool drive to the trocar.

Systems and methods of docking of robotic arms to trocars are needed that obviate the challenges presented by some modalities of trocar docking. In one aspect, a visual sensor system or imaging system, for example, one or more cameras positioned on the tool drive or elsewhere on the robotic arm, produce a sequence of digital images that capture the trocar. These images are processed by a data processor to determine a position and orientation of the trocar, i.e., a pose of the trocar, relative to the position and orientation of the camera and the tool drive. In response, the robotic arm is guided (its actuators are driven) by a surgical robotic arm control system, until the docking interface is aligned with and is at the position of the trocar, at which point mechanical coupling of the two can be achieved.

In one aspect, a surgical robotic system has a robotic arm with several joints and associated joint actuators, and a tool drive coupled to a distal end of the robotic arm. The tool drive has a docking interface to receive an attachment portion of a trocar. The system also has one or more sensors that are operable to visually sense a surface feature of the trocar. The one or more sensors can include an imaging sensor, for example, as part of an imaging system, e.g., a camera. In one variation, the imaging sensor can be disposed in a chamber of the docking interface. In another variation, a sterile adapter is coupled to a frontal portion of the docking interface, and the imaging sensor is mounted on the sterile adapter.

One or more processors are configured to determine a position and an orientation of the trocar by interpreting the sensed surface feature of the trocar. In other words, the processor determines a sensed pose of the trocar, based on digital image processing (including pattern recognition) of the image sequence produced by the imaging sensor. In one variation, the surface feature of the trocar is an encoded data payload that is detected and interpreted as being indicative of the sensed pose of the trocar.

Once the sensed pose of the trocar has been determined, the processors control the robotic arm actuators to guide the arm as the docking interface is moved towards the attachment portion of the trocar. The arm is guided by the processor driving the actuators, so as to orient the docking interface to the determined orientation of the attachment portion of the trocar. In one aspect, the arm is also guided by the one or more processors driving the actuators so as to move the docking interface to the determined position of the attachment portion of the trocar.

The one or more processors can be configured to generate a planned trajectory, between the current position of the docking interface of the tool drive and one or more of the sensed position of the trocar and the sensed orientation of the trocar. The planned trajectory is a path along which the docking interface of the tool drive can travel and reorient itself (as the arm is being guided by the control system), until the pose of the docking interface matches the sensed pose of the trocar (resulting in a docked state.)

In one variation, the robotic arm is automatically and fully driven along the planned trajectory, by the actuators (controlled by the one or more processors). In that case, there is no need for an operator to manually force the arm (to move along the trajectory). In another variation, the robotic arm is manually guided (forced by a hand of the operator) while being assisted by the actuators (that are controlled by the one or more processors). In still another variation, the robotic arm is manually guided by the operator along the planned trajectory, and the actuators controlled by the one or more processors resist the operator's manual guidance of the robotic arm whenever the operator's manual guidance is directing or causing the robotic arm to deviate (and in particular the docking interface) away from the planned trajectory. In that case, the actuators resist the operator's manual guidance of the robotic arm with a force that may be proportional to the distance between the docking interface and the planned trajectory (or how far off the docking interface is from the planned trajectory). This is also referred to here as a virtual spring mode of operation.

The docking interface can define a chamber, and a receiving space between one or more clamp components that are positioned in the chamber. In one variation, the one or more clamp components is movably coupled to the docking interface and configured to move to secure the attachment portion of the trocar, such as an upper protrusion, within the chamber of the docking interface. In another variation, a lever is supported on the docking interface, and movement of the lever (e.g., forced by the operators hand) causes movement of the one or more clamp components toward a locked or unlocked position that rigidly secures the attachment portion of the trocar to the docking interface. In still another variation, a switch is provided that, when actuated, signals the processors to activate one or more sensors, and/or to determine the position and orientation of the trocar based on the sensed surface feature of the trocar, and to then drive the actuators in order to guide the docking interface toward the determined orientation and position of the trocar. The switch can be positioned such that movement of the same lever, that is used to latch the docking interface to the trocar, also actuates the switch.

According to the present disclosure, a method for docking a robotic arm of a surgical robotic system to a trocar includes the following operations (performed in part by one or more processors). An image of a surface feature on the trocar captured by a sensor that is coupled to the robotic arm (e.g., coupled to a docking interface of a tool drive of the arm), is received. In one variation, the surface feature can be an encoded data payload. The processor determines a sensed pose of the trocar based on digital image processing of the image (e.g., detection and interpretation of the sensed surface feature). The sensed pose may include a position and orientation of the trocar, e.g., 6 degrees of freedom (DOF) including 3 DOF with regard to position and 3 DOF with regard to orientation. The sensed trocar pose may be computed in relation to a known pose of the docking interface, where the latter may have been determined using sensors and using a history of previously movement of the arm.

In addition, the one or more processors calculate a planned trajectory for the docking interface to travel and rotate until it matches the sensed trocar pose. The one or more processors then drive the actuators in the robotic arm, to guide the robotic arm (its docking interface) toward the sensed pose of the trocar, along the planned trajectory. The robotic arm can be guided under processor control in different ways. For example, the guidance may be fully automatic (no operator forcing of the arm needed) until the arm (its docking interface) has docked with the trocar. Alternatively, the processor control can assist the operator's manual force applied to the arm to reduce operator effort required to move the arm, or it may resist the operator's manual force whenever the arm leaves the planned trajectory.

In one variation, the processor determines a distance from the docking interface to the planned trajectory. Based on this distance, the processor drives the actuators in the robotic arm to guide the robotic arm toward the planned trajectory (e.g., moves the docking interface back to the planned trajectory, also referred to here as a course correction). Such driving of the robotic arm back toward the planned trajectory can be initiated according to a virtual spring modeled by the processor, in which a force applied to the robotic arm by the actuators (under control of the processor) is proportional to the distance from the docking interface to the planned trajectory.

In one aspect of the disclosure, the processor determines a component of a manual force that is being applied by an operator to the robotic arm along the planned trajectory, for example, through signals received from force and/or torque sensors in the robotic arm. The actuators in the robotic arm are then be driven so that the robotic arm is guided along the planned trajectory based on this component of the manual force applied by the operator along the planned trajectory, thereby assisting the operator's manual force. In one variation, the actuators are driven so that the robotic arm is guided with a force that is determined by the processor based on a product of the component of the manual force applied by the operator along the planned trajectory and a predetermined scalar value.

In another aspect of the disclosure, the processor determines a component of the operator's manual force, which is being applied by an operator to the robotic arm, directed away from the planned trajectory (again detected by signals received from force/torque sensors in the arm). The actuators in the robotic arm are then driven based on this component, so that the arm resists the manual force (which is directed away from the planned trajectory). In other words, the actuators are driven to produce a force on the arm that opposes the manual force, and it may be determined by the processor by computing a product of the component of the manual force applied by the operator away from the trajectory and a predetermined scalar value.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. Also, in the interest of conciseness and reducing the total number of figures, a given figure may be used to illustrate the features of more than one embodiment of the invention, and not all elements in the figure may be required for a given embodiment.

DETAILED DESCRIPTION

Several embodiments of the invention with reference to the appended drawings are now explained. Whenever the shapes, relative positions and other aspects of the parts described in the embodiments are not explicitly defined, the scope of the invention is not limited only to the parts shown, which are meant merely for the purpose of illustration. Also, while numerous details are set forth, it is understood that some embodiments of the invention may be practiced without these details. In other instances, well-known circuits, structures, and techniques have not been shown in detail so as not to obscure the understanding of this description.

Figure 1:
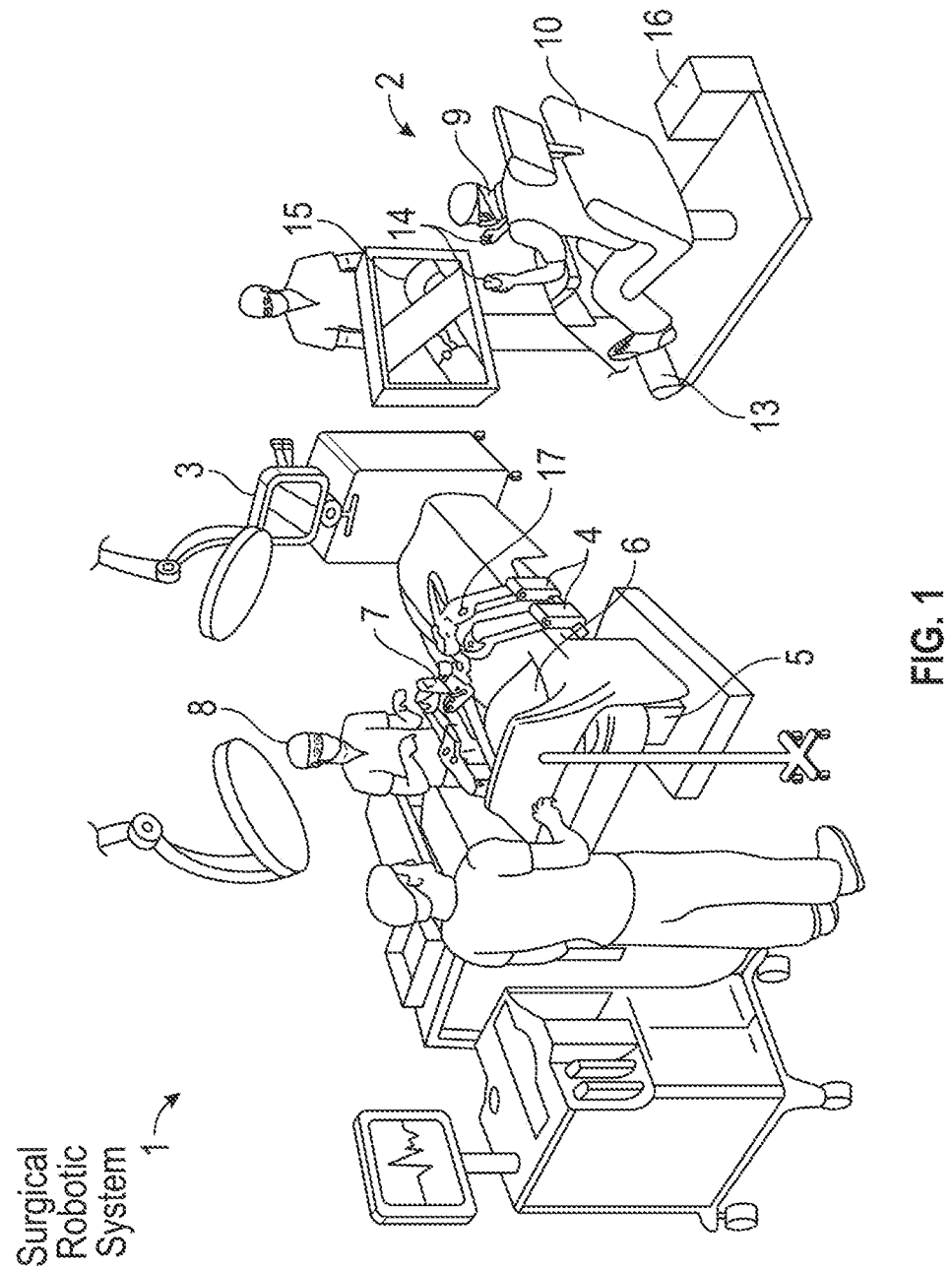
FIG. 1 is an overview schematic of an operating room arrangement with a surgical robotic system.

Referring to FIG. 1, this is a pictorial view of an example surgical robotic system 1 in an operating arena. The robotic system 1 includes a user console 2, a control tower 3, and one or more surgical robotic arms 4 at a surgical robotic platform 5, e.g., a table, a bed, etc. The system 1 can incorporate any number of devices, tools, or accessories used to perform surgery on a patient 6. For example, the system 1 may include one or more surgical tools 7 used to perform surgery. A surgical tool 7 may be an end effector that is attached to a distal end of a surgical robotic arm 4, for executing a surgical procedure.

Each surgical tool 7 may be manipulated manually, robotically, or both, during the surgery. For example, the surgical tool 7 may be a tool used to enter, view, or manipulate an internal anatomy of the patient 6. In an embodiment, the surgical tool 7 is a grasper that can grasp tissue of the patient. The surgical tool 7 may be controlled manually, by a bedside operator 8; or it may be controlled robotically, via actuated movement of the surgical robotic arm 4 to which it is attached. The robotic arms 4 are shown as a table-mounted system, but in other configurations the arms 4 may be mounted on a cart, ceiling or sidewall, or in another suitable structural support.

Generally, a remote operator 9, such as a surgeon, may use the user console 2 to remotely manipulate the arms 4 and/or the attached surgical tools 7, e.g., teleoperation. The user console 2 may be located in the same operating room as the rest of the system 1, as shown in FIG. 1. In other environments however, the user console 2 may be located in an adjacent or nearby room, or it may be at a remote location, e.g., in a different building, city, or country. The user console 2 may comprise a seat 10, foot-operated controls 13, one or more handheld user input devices, UID 14, and at least one user display 15 configured to display, for example, a view of the surgical site inside the patient 6. In the example user console 2, the remote operator 9 is sitting in the seat 10 and viewing the user display 15 while manipulating a foot-operated control 13 and a handheld UID 14 in order to remotely control the arms 4 and the surgical tools 7 (that are mounted on the distal ends of the arms 4.)

In some variations, the bedside operator 8 may also operate the system 1 in an "over the bed" mode, in which the beside operator 8 is now at a side of the patient 6 and is simultaneously manipulating a robotically-driven tool (end effector as attached to the arm 4), e.g., with a handheld UID 14 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 8 may perform both robotic-assisted minimally invasive surgery and manual laparoscopic surgery on the patient 6.

During an example procedure (surgery), prior to initiating surgery with the surgical robotic system 1, the surgical team can perform the preoperative setup. During the preoperative setup, the main components of the surgical robotic system (platform 5 and robotic arms 4, control tower 3, and user console 2) are positioned in the operating room, connected, and powered on. The robotic arms 4 may be in a fully-stowed configuration with the arms 4 under the platform 5 for storage and/or transportation purposes. The surgical team can extend the arms 4 from their stowed position for sterile draping, e.g., covering one or more portions of the system 1, such as portions of the arms 4, with a sterile barrier to minimize, inhibit, or prevent the transmission of pathogens. After draping, the arms 4 can be partially retracted until needed for use. A number of conventional laparoscopic steps may then be performed including trocar placement into the patient's body and insufflation. For example, each trocar can be inserted with the aid of an obturator, into a small incision and through the body wall. The sleeve and obturator allow optical entry for visualization of tissue layers during insertion to minimize risk of injury during placement. The endoscope is typically placed first to provide hand-held camera visualization for placement of other trocars or other tools or equipment.

In one embodiment, the remote operator 9 holds and moves the UID 14 to provide an input command to drive one or more robotic arm actuators 17 in the robotic system 1 for teleoperation. The UID 14 may be communicatively coupled to the rest of the robotic system 1, e.g., via a console computer system 16. The UID 14 can generate spatial state signals corresponding to movement of the UID 14, e.g., position and orientation of the handheld housing of the UID, and the spatial state signals may be input signals to control motions of the robotic arm actuators 17. The robotic system 1 may use control signals derived from the spatial state signals, to control proportional motion of the actuators 17. In one embodiment, a console processor of the console computer system 16 receives the spatial state signals and generates the corresponding control signals. Based on these control signals, which control how the actuators 17 are energized to drive a segment or link of the arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The surgical robotic system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn drives other linkages, gears, etc., of the robotic system 1. The robotic system 1 may include a right arm 4 that is secured to the bed or table to the right side of the patient, and a left arm 4 that is at the left side of the patient. An actuator 17 may include one or more motors that are controlled so that they drive the rotation of a joint of the arm 4, to for example change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator that opens or closes jaws of the grasper at a distal end of surgical tool 7 to grip tissue within patient 6.

In some aspects, the communication between the platform 5 and the user console 2 may be through a control tower 3, which may translate user commands that are received from the user console 2 (and more particularly from the console computer system 16) into robotic control commands that are transmitted to the arms 4 on the robotic platform 5. The control tower 3 may also transmit status and feedback from the platform 5 back to the user console 2. The communication connections between the robotic platform 5, the user console 2, and the control tower 3 may be via wired and/or wireless links, using any suitable ones of a variety of data communication protocols. Any wired connections may be optionally built into the floor and/or walls or ceiling of the operating room. The robotic system 1 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

As described above, to create a port for enabling introduction of a surgical instrument into the patient 6, a trocar assembly may be inserted into the patient through an incision or entry point in the patient (e.g., in the abdominal wall). The trocar assembly may include a cannula or trocar 63 (FIG. 6), an obturator, and/or a seal. In some variations, the trocar assembly can include an obturator such as a needle with a sharpened tip for penetrating through a patient's skin.

It will be understood that the trocar 63 as described herein includes at least a cannula, and can optionally include an obturator or other components. The obturator may be disposed within the lumen of the trocar 63 when being inserted into the patient 6, and then removed from the trocar 63 such that a surgical instrument may be inserted through the lumen of the trocar 63. Once positioned within the body of the patient 6, the trocar 63 may provide a channel for holding therein one or more surgical tools inside a body cavity or other site within the patient 6, and for the docked arm 4 to move the tools during teleoperation.

Figure 2:
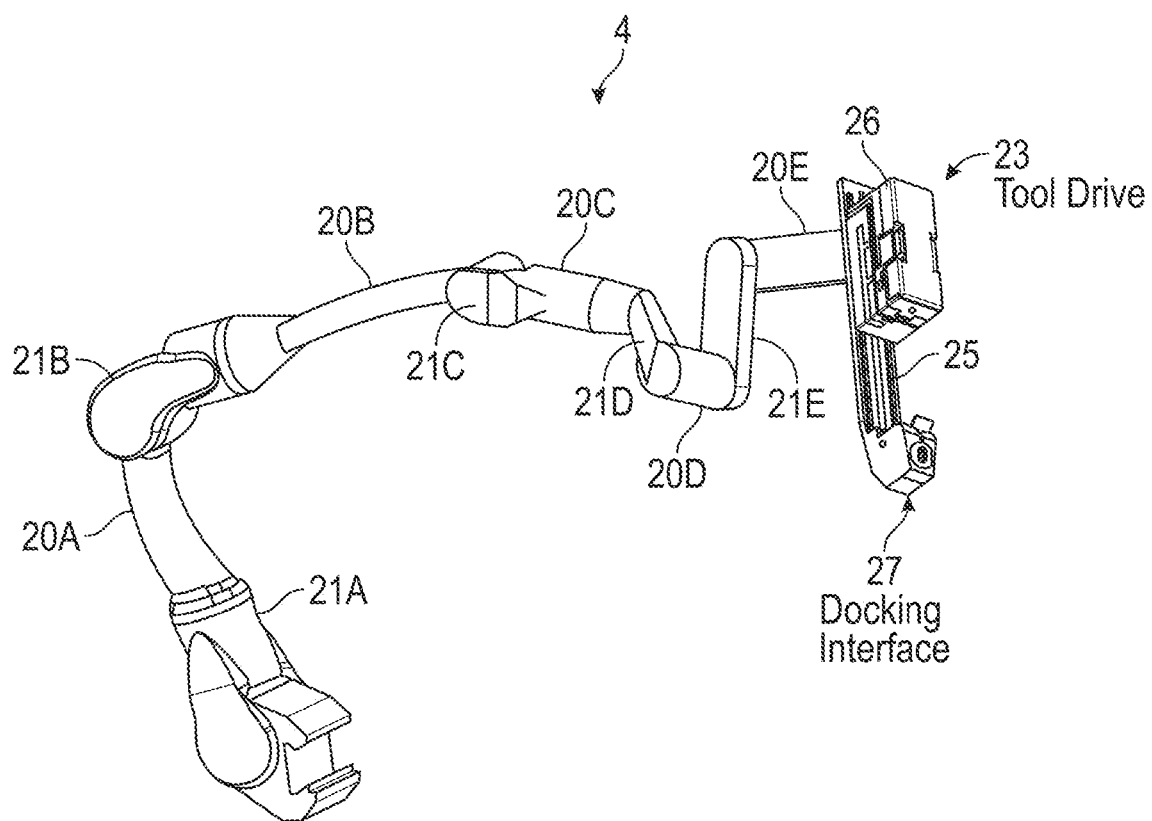
FIG. 2 is a perspective view of a portion of a robotic arm according to one aspect of the disclosure.

Turning to FIG. 2, a portion of an example robotic arm 4 is illustrated according to one aspect of the disclosure. The robotic arm 4 can include a plurality of links (e.g., links 20A—20E) and a plurality of joint modules (e.g., joints 21A-21E) for actuating the plurality of links relative to one another. The joint modules can include various joint types, such as a pitch joint or a roll joint, any of which can be actuated manually or by the robotic arm actuators 17, and any of which may substantially constrain the movement of the adjacent links around certain axes relative to others. As also shown, a tool drive 23 is attached to the distal end of the robotic arm 4. As described herein, the tool drive 23 can be configured with a docking interface 27 to receive an attachment portion (e.g., a mating interface) of a trocar 63 such that the trocar 63 can then be rigidly secured to the robotic arm 4. In that condition, the distal, elongated portions of one or more surgical instruments (e.g., endoscopes, staplers, etc.) can be guided through a lumen of the cannula of the trocar 63, and the instruments can be attached to the tool drive. The plurality of the joint modules 21A-21E of the robotic arm 4 can then be actuated under control of the control system, to position and orient the arm 4, the tool drive 23 and thus the attached surgical instrument, for teleoperation during robotic surgery.

Figure 3:
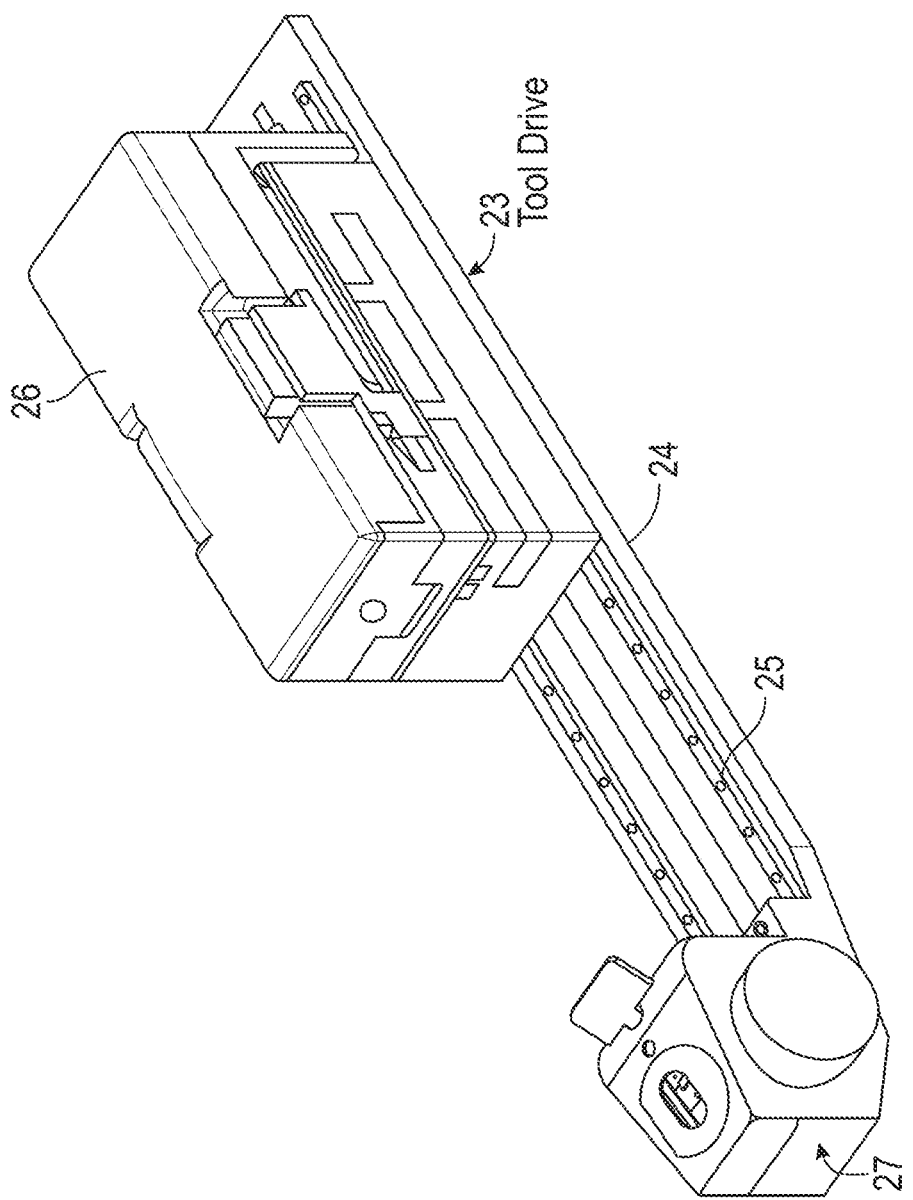
FIG. 3 is a schematic perspective view of a tool drive of the robotic arm of FIG. 2.

FIG. 3 is a schematic diagram illustrating an exemplary tool drive 23, without the tool 7 having been loaded, in accordance with aspects of the subject technology. In one variation, the tool drive 23 may include an elongated base (or "stage") 24 having longitudinal tracks 25 and a tool carriage 26, which is slidingly engaged with the longitudinal tracks 25. The stage 24 may be configured to couple to the distal end of the robotic arm 4 such that articulation of the robotic arm 4 positions and/or orients the tool drive 23 in space. The tool carriage 26 may be configured to receive the tool 7 (whose distal portion is to be inserted through the trocar 63). Once the tool 7 has been attached to the tool carriage 26, the latter may actuate a set of articulated movements of the tool 7 (as the end effector) through any suitable mechanical transmission, e.g., a system of cables or wires and/or gears, by actuators in the tool carriage 26 that are driven by the control system.

Figure 4:
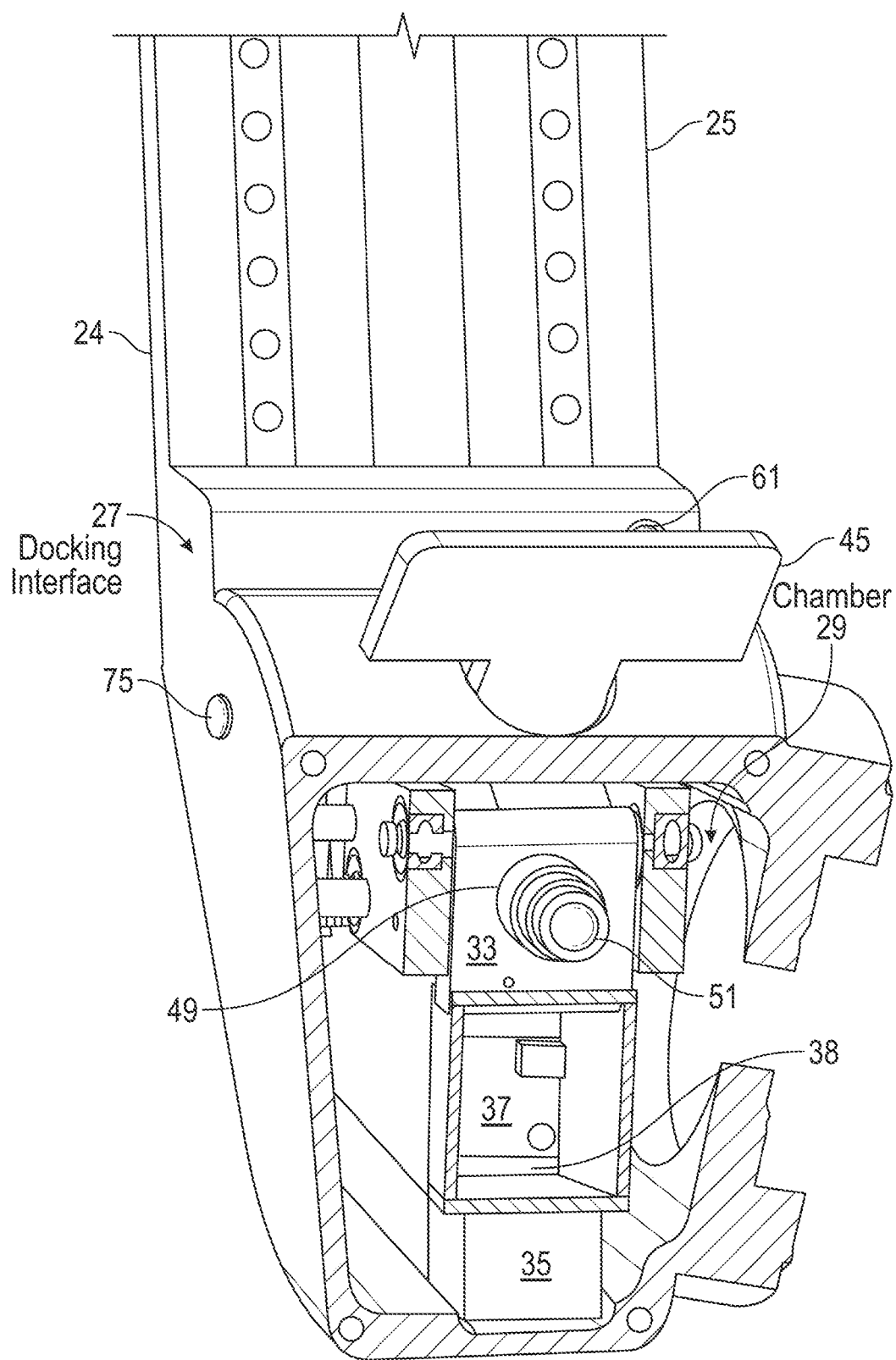
FIG. 4 is a perspective view of a cross-section of a docking interface of the tool drive of FIG. 3 and including a sensor system.
Figure 5:
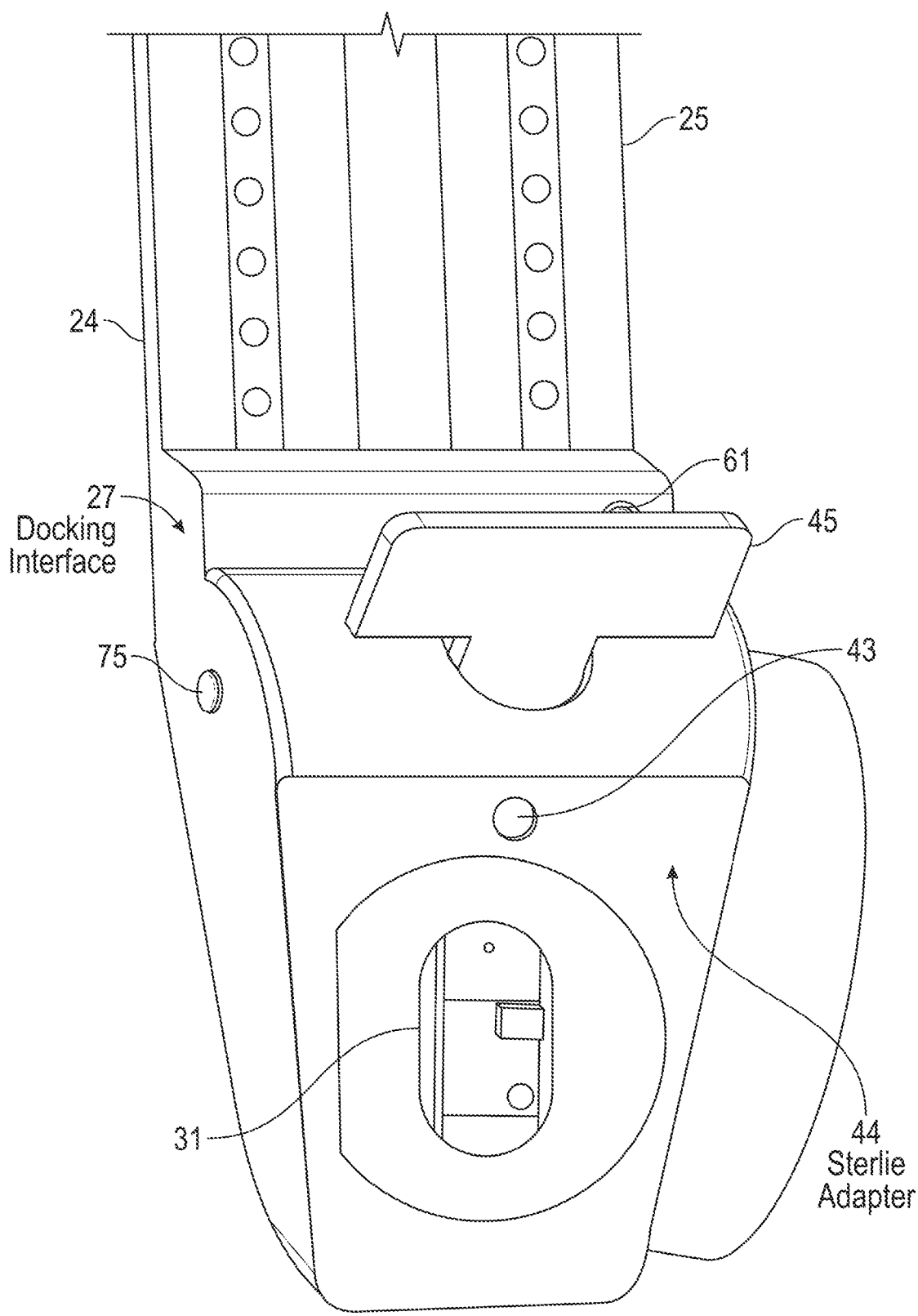
FIG. 5 is a perspective view of a docking interface of the tool drive of FIG. 3 and including a sensor system according to one variation of the disclosure.

Referring additionally to FIGS. 4 and 5, the trocar 63 can be coupled to the tool drive 23 or another component of the surgical robotic system 1 at a docking station or docking interface 27 located at a distal block of the elongated base 24 as also seen for example in FIG. 4. The docking interface 27 is configured to receive a portion of the trocar 63 such that the docking interface 27 is configured as a trocar docking interface, a trocar attachment device, or a trocar mounting device. The docking interface 27 can provide a reliable and quick way to attach the trocar 63 to the surgical robotic arm 4.

As seen in FIG. 4, the docking interface 27 can define a chamber 29 that is accessible through its mouth or frontal opening 31 (see FIG. 5) of the docking interface 27 and which can include first and second clamp components 33, 35

(e.g., arms, plates, levers, members) arranged about a receiver 37 that defines a receiving space 38 therein for receiving a portion of the trocar 63 (e.g., a mating interface, such as an attachment portion of a cannula located in a proximal portion of the cannula). At least one of the clamp components 33, 35 may be pivotable between an open position and a closed position; in the closed position, an attachment portion 69 (see FIG. 6) of the trocar 63 (which has been inserted into the receiving space 38 between the clamp components 33, 35) is held in place at least partially by the first and second clamp components 33, 35.

In one variation, the docking interface 27 may include an over-center mechanism that includes a lever 45 or other suitable locking component that mechanically cooperates with the clamp component 33, for example, through a pin and slot arrangement or through another pivotable or movable connection, between the open and closed positions. The lever 45 can be movable, e.g., along a track or slot defined in a body or housing of the docking interface 27, between a forward, locked position (e.g., a locked over-center position) and a rearward, unlocked position. When the lever 43 is moved toward the locked position, the lever 45 may urge the clamp component 33 downwardly toward the receiving space 38 and lock the clamp component 33 in the closed position such that a portion of the trocar 63 is securely held between the first and second clamp components 33, 35. In some variations, second clamp component 35 can be stationary or can be fixed. In one variation, the lever 45 can be driven by an electric motor or actuator (controlled by a processor or by a switch that is under operator manual control), or it may be driven by manual force of an operator's hand.

As seen in FIG. 5, the docking interface 27 may also provide a sterile barrier between sterile components such as the trocar 63 and non-sterile components such as the first and second clamp components 33, 35 (or other non-sterile components of the surgical system). The sterile barrier may be provided, for example, by a sterile adapter 44 formed of a surgical-grade polymer or other surgical-grade material that is interposed between the trocar 63 and the first and second clamp components 33, 35. In this regard, the sterile adapter 44 can be coupled to a frontal portion of the docking interface 27 such that a hole in the sterile adapter 44 is aligned with the mouth of frontal opening 31 of the docking interface 27, as seen in FIG. 5. The attachment portion 69 of the trocar (see FIG. 6) is to pass through that hole and then through the frontal opening 31 before being positioned inside the receiving space 38 of the chamber 37.

A sensor system is provided, for example in the docking interface 27 as seen in FIG. 4 and FIG. 5, that may be at least partially recessed in the chamber 29 or can be otherwise coupled to or supported by the docking interface 27. The sensor system can include an imaging sensor 49 and a lens 51. The sensor system can produce a sequence of digital images (e.g., video), that capture the scene within the field of view of the lens 51 that is front of the docking interface 27 as shown. The lens 51 may be a polymeric or composite element that can provide protection to the imaging sensor 49 from, for example, fluids, particulates, or incidental contact with an operator or surgical equipment. The imaging sensor 49, and, optionally, the lens 51, can be provided within an additional enclosure (not shown) to provide additional impact or vibrational protection, particulate or fluid resistance, etc. As seen in FIG. 5, the sensor system may be covered by the sterile adapter 44 in which a protective cover portion 43 that is transparent to visible light is positioned over the front surface of the lens 51 (to allow the sensor system to view the scene in front of the docking interface 27).

The sensor system may be positioned such that the lens 51 is positioned entirely within the chamber 29 (and as such does not protrude from the front most plane of the docking interface 27. The sensor system should be mounted to the docking interface 27 so as to not obstruct or interfere with other operations of the docking interface 27, for example, movement of the lever 45 and movement of one or more of the clamp components 33, 35, as described above, as well as receipt of one or more portions of a trocar 63.

Although not shown in FIG. 5, there may also be a sterile drape or barrier that is attached to the robotic arm 4 at portions spaced away from the docking interface 27, and that covers the docking interface 27 to maintain a sterile barrier with the trocar 63, and has a visible light portion that is aligned with the imaging path surface of the lens 51 to provide the sensor system with an unobstructed view of the scene in front of the docking interface 27.

A processor or controller that may be part of the control tower 3 (see FIG. 1) will process a digital image sequence produced by the sensor system, to determine how to guide the arm 4 (by providing driving commands, for example, force or velocity commands to various actuators 17 in the arm 4), so as to direct a movement of the docking interface 27. It will be understood that such a processor could be part of other portions of the surgical robotic system 1, where the sensor system 47 is in electrical communication with one or more of such processors. Also, such processing may be triggered by actuation of a switch 61 or other user selectable control that is mounted on the arm 4, e.g., on the tool drive 23, and in particular on the docking interface 27 as shown in FIG. 5, for example. The switch 61 in that case is positioned behind the lever 45 at a position such that the lever 45 can be urged into contact with, and to thereby actuate, the switch 61, as described further herein. The switch 61 is in electrical communication with the processor in the control tower 3, and when actuated signals the processor to energize or activate the sensor system and/or to start processing the image data produced by the sensor system to determine a planned trajectory for guiding of the robotic arm 4 (and its attached tool drive 23) toward the trocar 63 according to an algorithm, as described further herein. The switch 61 is used generically here to refer to any suitable mechanism that can be triggered by an operator, e.g., a momentary mechanical switch, a proximity sensor, a virtual switch as part of a touchscreen or touchpad, etc. Placement of the switch 61 on or near the docking interface 27 ensures that the operator activates the sensor system to guide the docking interface 27 only while in proximity with the arm 4 and without the need for a separate control interface (for example, via the user console 2 which may be located too far away from the robotic arm 4 to allow an operator who is seated at the user console 2 to see how the docking interface 27 is moving toward the trocar 63).

Referring additionally to FIGS. 6-9, guidance and docking of the docking interface 27 of the tool drive 23 with a trocar 63 that is at least partially inserted into the patient 6 (and is preferably kept there at a constant pose) is illustrated according to one aspect of the disclosure. The trocar 63, as shown, includes a generally tubular body 64 with a flanged upper portion or head 67 and an attachment portion 69 that protrudes from the head 67 for mating with the docking interface 27. In one variation, the attachment portion 69 can be configured, for example, as having a nose or collar or pin-like arrangement, and can have one or more surface features, e.g., notches, ridges, protrusions, angles, hooks, etc., for inter-engaging the receiver 37 of the docking interface 27. The trocar 63 can have a different arrangement without departing from the disclosure. A target marking or surface feature 71, e.g., a textured surface, marking, printing, or other visible indicia, can be provided on an upper portion of the trocar 63, for example, a side of the head 67 of the trocar 63. The surface feature 71 can be, for example, etched, stamped, printed, or provided as an attachment such as a sticker or label, and can have an arrangement corresponding to an encoded data payload. For example, the surface feature 71 can have the arrangement of a barcode or a two-dimensional barcode or matrix barcode that can include data such as numeric data, alphanumeric data, byte/binary data, or other data. In one variation, the surface feature can correspond to or provide a link to information that is associated with a particular algorithm for guiding or driving the robotic arm 4 and its docking interface 27 toward the trocar 63. The control system may load such an algorithm in response to detecting the surface feature, and execute the algorithm for guiding the robotic arm 4 and its docking interface 27 towards the trocar 23. The trocar 63, and the surface feature 71 thereof, can have a different arrangement without departing from the disclosure. For example, in another variation, the surface feature 71 can itself be the visible attributes of the outer structure of one or more portions of the trocar 63, e.g., its shape, dimensions, etc.

Figure 6:
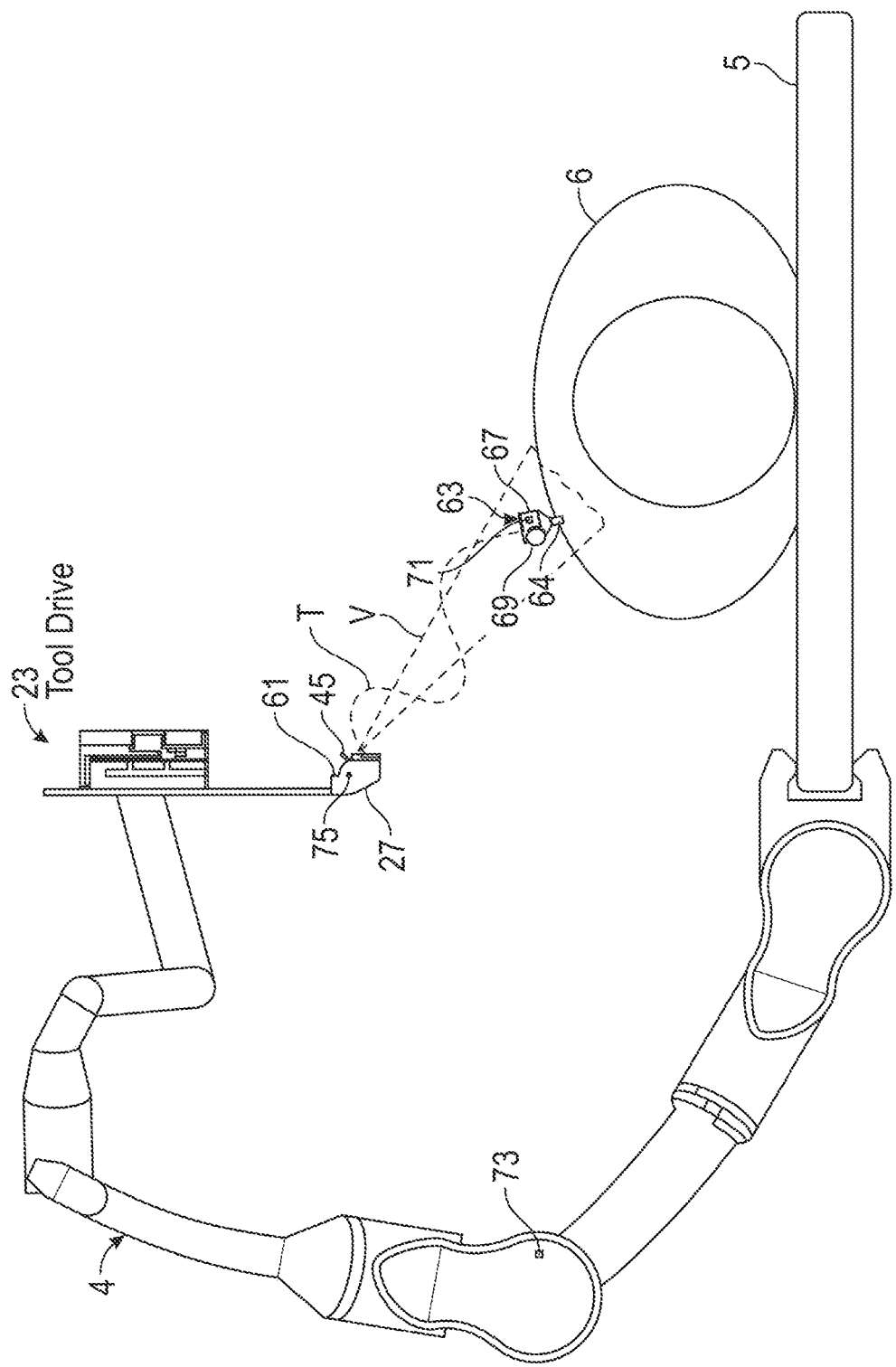
FIGS. 6-8 are pictorial views of operations of a method of docking a tool drive attached to a robotic arm of a surgical robotic system to a trocar according to one aspect of the disclosure.
Figure 7:
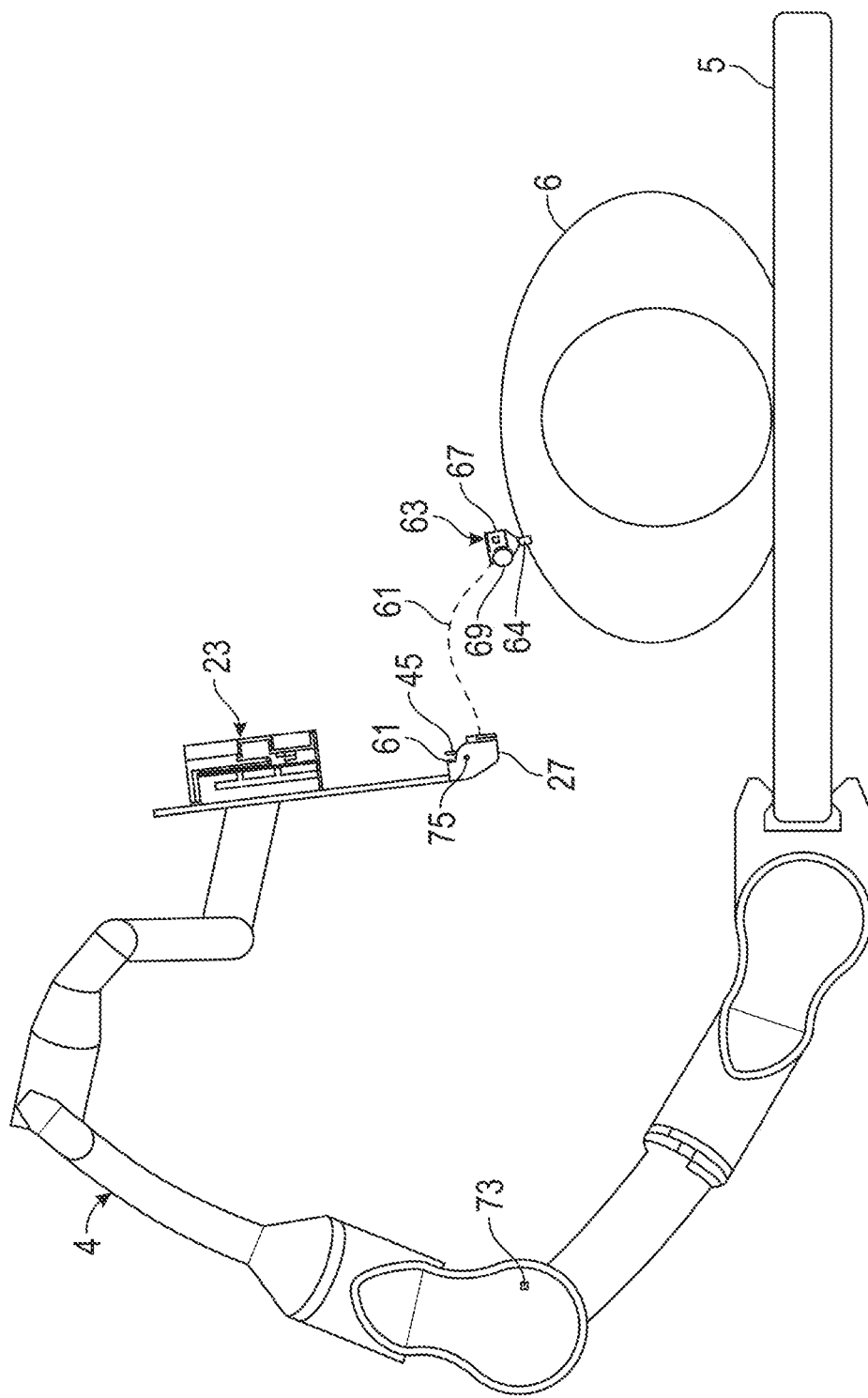

The docking interface 27 of the robotic arm 4 can be guided from a first pose (e.g., a parked pose, or an unknown pose) to a second pose illustrated in FIG. 6 that is proximate, but physically separate from the trocar 63. Such guidance may be, for example, manual forcing by an operator, or it may be driving by the robotic arm actuators 17. In the second pose, the robotic arm 4/docking interface 27 is positioned such that the trocar 63 is within a field of view V of the sensor system 47. The field of view V can include a direct line of sight to at least a portion of the trocar 63. In one variation, a suitable proximity or arrangement of the robotic arm 4/docking interface 27 relative to the trocar 63 can be indicated to an operator (by the processor), for example, as an audible beep or audible alarm, an indicator light or other visual indicia, and/or a tactile indicator such as haptic or vibratory feedback on a portion of the robotic arm 4. In this regard, the imaging sensor 49 can be activated by the processor, for example upon an initial setup or preparation of the robotic arm 4 and the tool drive 23, or via an input by an operator, prior to positioning of the robotic arm 4/tool drive 23 into the second pose. If the docking interface 27 is not in suitable proximity to the sensor system 47 (to establish a field of view V that encompasses the trocar 63), then the robotic arm 4 can be further guided toward the trocar 63, for example, by manual forcing by the operator, by automatic guidance under control of the processor, or some combination thereof, until determination by the processor that the trocar 63 is positioned within a field of view of the sensor system 47. FIG. 7 shows how the arm 4 has moved closer to the trocar 63 (as compared with the initial pose of FIG. 6).

Figure 8:
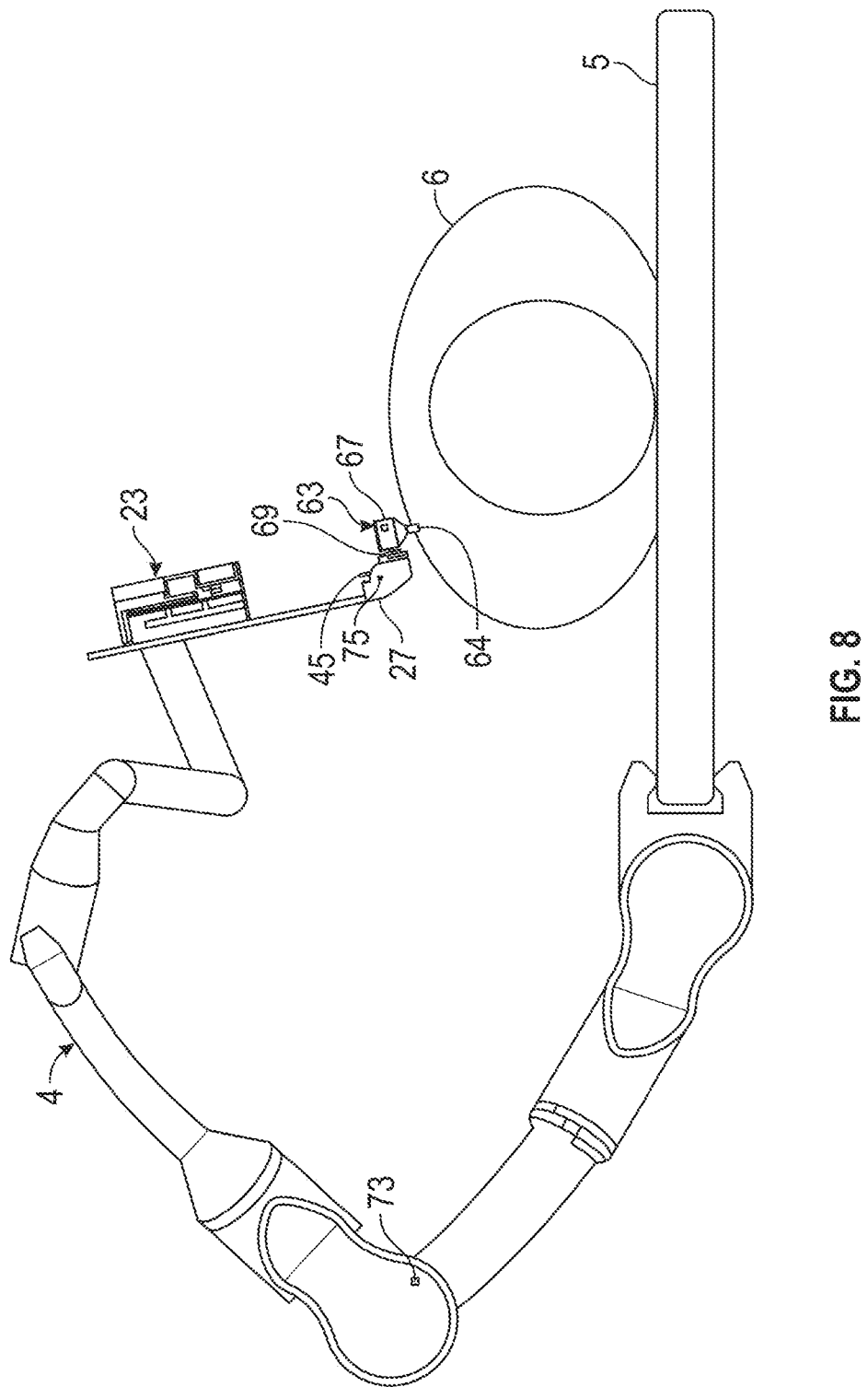
Figure 9:
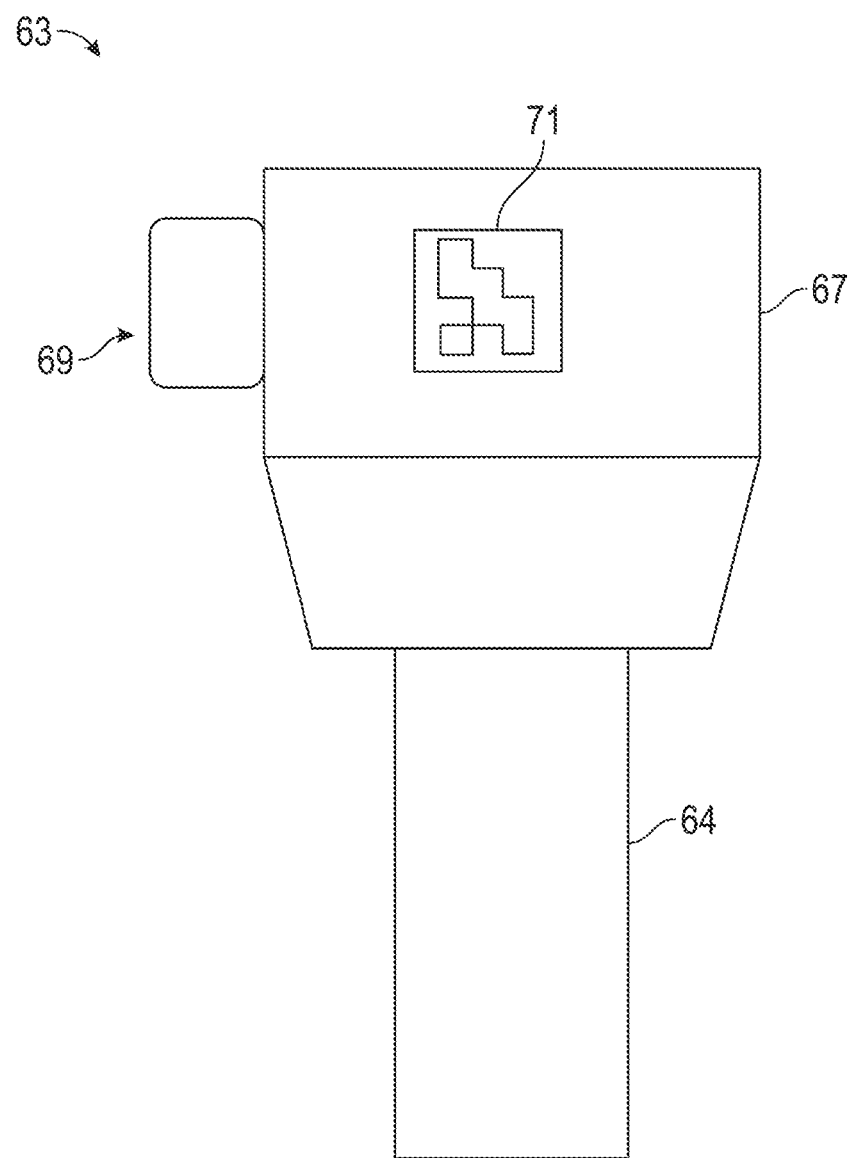
FIG. 9 is an enlarged schematic of the area 9 identified in FIG. 6.

The docking interface 27 and in particular the sensor system 47 is positioned and oriented to receive light from the field of view V and in response produces corresponding image data electrical signals that are communicated to the processor in the control tower 3. The processor calculates a position and orientation of the trocar 63 relative to the docking interface 27 by analyzing the image data, e.g., upon identification of the surface feature 71 of the trocar 63 according to an object recognition algorithm. The initialization or start of such algorithm can be prompted, for example, by activating the switch 61. In one variation, the switch 61 can be activated by moving the lever 45 rearward into the unlocked (rearward) position such that the lever 45 contacts and actuates the switch 61. Accordingly, the processor in the control tower 3 is signaled by the switch 61 to apply an algorithm to determine the pose, e.g., spatial position and orientation, of the attachment portion 69 of the trocar 63 relative to the docking interface 27. The processor may thus compute a transform, e.g., a transformation matrix, that can be used to guide or drive the robotic arm 4, and the docking interface 27 of the tool drive 23 attached thereto, toward the trocar 63. In this regard, the processor generates a planned trajectory for the robotic arm 4/docking interface 27 along which the robotic arm 4/docking interface 27 should move and reorient to arrive at a pose that matches the pose of the trocar 63 sensed by the sensor system 47 (as seen in FIG. 8 where the docking interface 27 is shown as having arrived, or docked, inside the head 67 of the trocar 63). Note that "matching" as used in this disclosure does not mean exactly the same but rather to within a tolerance. The algorithm can be a set of computer-implemented instructions, e.g., as part of a computer program product, firmware, etc., that can be stored on a non-transitory computer-readable medium for processing by a processor of the control tower 3, and will be collectively referred to as an algorithm herein. The initialization of the algorithm by the processor can be considered a start of a docking procedure for the robotic arm 4 or the attached tool drive 23.

The object recognition algorithm applied by the processor can be, for example, a feature-based or object recognition algorithm that recognizes the surface feature 71 or other feature of the trocar 63 within the field of view V of the sensor system 47. Such an algorithm can include, for example, a Harris affine region detector or a scale-invariant feature transform (SIFT). In one variation, in the presence of multiple trocars, the processor can uniquely identify and distinguish the trocar 63 via identification of the surface feature 71 according to the algorithm, where each trocar is provided with a unique surface feature. In an environment with multiple robotic arms, each robotic arm 4 can be designated to identify a predetermined surface feature 71. In one aspect, the processor determines a pose of the attachment portion 69 of the trocar 63 by analyzing the image data output by the sensor system 47 to determine one or more of a depth distance, e.g., X-axis distance, between the trocar 63 and the docking interface 27, a horizontal distance, e.g., Y-axis distance, between the trocar 63 and the docking interface 27, a vertical distance, e.g., Z-axis distance, between the trocar 63 and the docking interface 27, and rotational orientation about one or more of the X-, Y-, and Z-axes.

Once the surface feature 71 has been identified and on that basis the pose of the trocar 63 has been computed, a tracking path or a planned trajectory T for the robotic arm 4/docking interface 27 to follow toward the attachment portion 69 of the trocar 63 can be generated by the processor in the control tower 3. The planned trajectory T can be generated by the processor based at least upon the image data received from the sensor system 47. In one variation, at least a portion of the planned trajectory T can include a pre-determined path generated independently of the image data from the sensor system 47. In this regard, the planned trajectory T may start from a known pose of the docking interface 27 and may be computed based on a log of prior movements, signals received from the F/T sensor 73, or other inputs. The planned trajectory T may be designed to navigate around one or more objects that may be between the robotic arm 4/docking interface 27 and the trocar 63, and to enable the docking interface 27 to match the sensed pose of the trocar 63. In this regard, the planned trajectory T can provide a path that goes around and therefore avoids collisions with, for example, portions of the patient's anatomy, the surgical platform on which the patient is resting, bedside staff, cables or pipes, additional robotic arms, or other surgical equipment or other personnel in the operating environment. The planned trajectory T can be provided with respect to a 3-axis coordinate system, such as a system of mutually-perpendicular X-, Y-, and Z-axes, and can include translational movement along one or more of the X-, Y-, and Z-axes, as well as rotational orientation about one or more of the X-, Y-, and Z-axes, e.g., roll, pitch, and yaw. While the planned trajectory T is illustrated as a curvilinear line in the figures, it will be understood that the planned trajectory T can include one or more straight, angled, or discontinuous portions, and can be provided in one or more segments or stages.

As described herein, guidance of the robotic arm 4 along the planned trajectory T toward the trocar 63 can be accomplished according to several modalities. For example, in one variation, the robotic arm 4/docking interface 27 is guided to dock with the trocar 63 under an at least partially automated process in which the processor in the control tower 3 drives the robotic arm actuators 17 to guide the robotic arm 4/docking interface 27 in response to sensing manual forcing or guidance by an operator. Such guidance may be achieved using a control algorithm which may include admittance control, in which external forces exerted on the robotic arm 4 (e.g., gravity, and an operator's manual force) are sensed, and together with measured joint positions and joint velocities as feedback are used by the algorithm in determining commands that drive the robotic arm actuators 17. In this regard, the robotic arm 4 can include an F/T (force/torque) sensor 73 to receive, as inputs, forces or torques that have been manually exerted, on the robotic arm 4 by an operator, and produce corresponding electrical signals as outputs, to the processor in the control tower 3. The F/T sensor 73 can also receive, as inputs, forces exerted on the robotic arm 4 by the robotic arm actuators 17. Accordingly, the F/T sensor 73 can be configured to receive, as inputs, linear forces or rotational forces, e.g., torque. While the F/T sensor 73 is schematically shown as being mounted or integrated at a particular joint of the robotic arm 4, there may more than one such F/T sensor 73 that can be integrated into various joints or other portions of the robotic arm 4 without departing from this disclosure.

As described herein, guidance of the robotic arm 4/docking interface 27 toward the trocar 63 can be manually forced, at least in part, by an operator. However, due to the generally large forces required to manipulate the robotic arm 4 (e.g., due to weight, friction, etc.), manual guidance by an operator is assisted by the robotic arm actuators 17 under processor control. In one variation, the processor can generate or model a virtual spring for the guidance control algorithm that corrects or resists any manual forcing in directions that deviate from the planned trajectory T. Such a virtual spring generated by the processor dictates, according to a predetermined virtual spring constant (k), the amount and direction of forces needed on the robotic arm 4 that tend to return the robotic arm 4/docking interface 27 toward alignment with the planned trajectory T. These forces may be made to be proportional to a distance traveled away from the planned trajectory T (by a respective portion of the robotic arm 4/docking interface 27). In this regard, the virtual spring constant (k) is a predefined function that receives, as an input, the distance and direction of the docking interface 27 of the tool drive away from the planned trajectory T. In one variation, the processor can signal the robotic arm actuators 17 to counteract any manual forcing of the robotic arm 4/docking interface 27 that is a direction away from planned trajectory T.

In this regard, the operator can encounter a resistive force applied by the robotic arm actuators 17, according to the virtual spring generated by the processor, such that the resistive force increases with increasing distance from the planned trajectory T. In this regard, the processor in the control tower 3 provides the planned trajectory T as a virtual fixture, deviation from which results in corrective movements of and forces exerted on the robotic arm 4 by the robotic arm actuators 17 which tend to return the robotic arm 19/docking interface 27 toward an alignment with the planned trajectory T.

Additionally or alternatively, manual guidance of the robotic arm 4/docking interface 27 along the planned trajectory T can be assisted, e.g., augmented, amplified, enhanced, etc., by the robotic arm actuators 17. For example, manual forcing of the robotic arm 4/docking interface 27 by an operator in directions along the planned trajectory T, e.g., exactly along the planned trajectory T or proximate the planned trajectory T (within a predetermined tolerance), can be assisted by the robotic arm actuators 17. In that case, the processor receives, as an input, signals from the F/T sensor 73 corresponding to the forces applied to the robotic arm 4 by the operator, and in response drives the robotic arm actuators 17 to assist the manual guidance. Such assistive forces on the robotic arm 4/docking interface 27 provided by the robotic arm actuators 17 under processor control can be consistent with the spring constant (k) or can be at least partially based on a different factor, as described further herein.

Providing the aforementioned planned trajectory T/virtual fixture and the associated virtual spring modeled by the processor can significantly reduce effort by an operator in guiding the robotic arm 4/docking interface 27 toward the trocar 63 and in maintaining alignment of the robotic arm 4/docking interface 27 with the planned trajectory T. Two virtual fixture approaches are described below that can facilitate the docking process.

Assuming the surgical plan is known, e.g., the type of surgery, the size of the patient, the location and orientation of the patient on the table, and the location of a trocar inserted into the body of the patient, then the location of the head of the trocar including its attachment portion 69 can be estimated (as computed by the processor using a physical model). In such a case, the processor can guide the robotic arm 4 into proximity of the trocar 63, e.g., until reaching the second pose shown in FIG. 6. Alternatively, the processor may operate in a mode that allows the operator to manually force the arm 4 to the position shown in FIG. 6 (with only active gravity compensation and back driving to overcome friction in the joints of the arm 4). Once the robot arm 4 is in the position shown in FIG. 6, then any suitable sensing methodology may be performed by the processor to estimate more precisely the location of the trocar 63 (and in particular its attachment portion 69) relative to the arm 4 (and in particular its docking interface 27). Possible sensing methodologies here include magnetic sensing, structured light camera sensing, and, as described here, sensing by analyzing image data from a visible light camera. Once the robotic arm 4 reaches a suitable position where the sensing methodologies are expected to be effective in estimating the trocar location more precisely (computing a "sensed or measured pose" of the trocar 63), the processor may respond by providing an alert or feedback to an operator of the system as mentioned above using any of various techniques. At this point, the operator has the option of selecting one of at least two virtual fixture modes of operation, for the control system to assist the operator's manual guidance of the arm, to "fine tune" the pose of the robotic arm 4/docking interface 27 closer to docking and then actual docking (by driving the actuators 17 of the arm 4 to assist the manual guidance).

Figure 10:
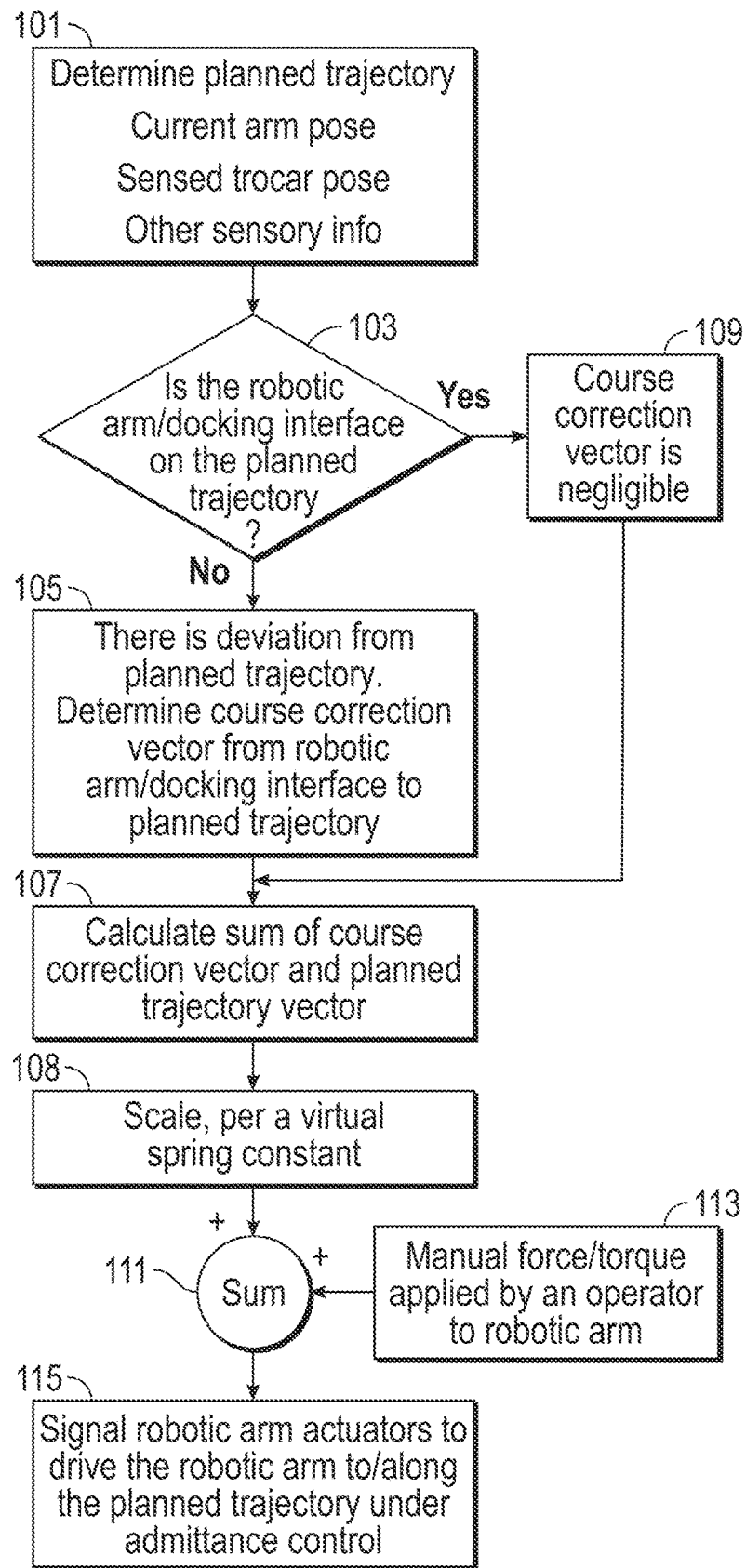
FIG. 10 is a process flow of a method for docking a tool drive attached to a robotic arm of a surgical robotic system to a trocar according to one aspect of the disclosure.

The selection between the two virtual fixture modes may be made by the bedside operator 8 pressing a button switch on the arm 4 or a foot pedal switch at the platform 5, which can activate a predetermined one of the virtual fixture modes or toggle between them. FIG. 10 is a process flow for an active virtual fixture mode, in which the processor automatically guides the arm 4, along the planned trajectory T, by suitably driving the actuators 17 of the arm 4 to affect movement of the arm 4 along the planned trajectory T. In one sub-mode referred to here as fully automatic, the processor controls the actuators 17 so that the docking interface 27 is automatically driven to approach and dock with the trocar 63 (along the trajectory T), without requiring any manual forcing by the operator. This sub-mode is useful as it allows fine tuning of the pose of the docking interface 27 when near docking. In another sub-mode of the active virtual fixture mode, the processor controls the actuators 17 to drive the arm 4 (generates movement of the arm 4) only to the extent needed to assist the operator's manual guidance—the processor controls the actuators 17 to pause the arm 4 in its last position in response to detecting that the operator has stopped manual forcing of the arm 4.

Referring to FIG. 10, a process flow for an active virtual fixture mode of operation is shown. In the active virtual fixture mode, the control system generates or drives movement of the arm 4 forward along the planned trajectory T. The processor generates the planned trajectory T (FIG. 10, block 101) according to an algorithm that plans at the joint level or at the task level. This algorithm determines a suitable path for the docking interface 27 to follow in order to arrive at the sensed or measured pose of the trocar 63 as depicted in FIG. 8. The sensed or measured pose of the trocar may have been determined by the processor analyzing the image data from the sensor system 47, or it may have been determined by the processor analyzing other sensor data produced by any other sensor system (while at the initial pose in FIG. 6). The planned trajectory T may be based upon one or more inputs as signals from other sensors, e.g., proximity sensors to detect nearby objects, accelerometers, and as information provided by an operator (for example, through the user console 2), and as parameters associated with the operating environment such as characteristics of the patient 6 (e.g., the size or shape of the patient) or characteristics of the platform 5 that supports the patient 6, etc. In one variation, the planned trajectory T may start from the current pose of the robotic arm 4/docking interface 27, which can be determined by the processor through signals received from the F/T sensor 73 or other sensor inputs, or it can be a known value, for example, as determined from a log of prior movements.

While the planned trajectory T has been described as an output from the processor in the control tower 3, it will be understood that one or more portions of the planned trajectory T can be manually input by an operator, e.g., received through a touchscreen.

Still referring to FIG. 10, at block 103, the processor determines whether or not the robotic arm 4/docking interface 27 is positioned along the planned trajectory T, e.g., based on a determined, current pose of the docking interface 27. If not, the processor determines distance and direction of the docking interface 27 from the planned trajectory T, e.g., as the distance and direction from a nearest point along the planned trajectory T (block 105). The planned trajectory T may have been provided as a series of incrementally-spaced points. The distance and direction may be referred to as a course correction vector having one or more of X-, Y-, or Z-components, or a sequence of vectors, and can represent a path along which the robotic arm 4/docking interface 27 can travel to become aligned with the nearest point of the planned trajectory T.

At block 107, the processor in the control tower 3 determines a virtual force/torque vector to be applied to the robotic arm 4 based upon the sum of the course correction vector and a planned trajectory vector of the planned trajectory T. This resulting sum vector may be scaled in block 108, based on the spring constant of a virtual spring modeled or generated by the processor. Such operation provides a virtual force/torque vector that is applied to the robotic arm 4 (by driving the robotic arm actuators 17), where such virtual force/torque vector will guide the robotic arm 4/docking interface 27 toward alignment with the planned trajectory T.

Returning to block 103, if the robotic arm 4/docking interface 27 is determined by the processor to be positioned along the planned trajectory T (i.e., within an acceptable tolerance), the processor determines that the course correction vector to be applied to the robotic arm 4 should be negligible or zero at block 109.

Arriving then at block 111, a summation of i) the virtual force/torque vector as determined by the processor in block 108 and ii) the detected manual force/torque vector that is being applied by the operator on the robotic arm 4 (for example, as detected by the processor based on signals from one or more F/T sensors 73, illustrated as block 113) is performed (by the processor). It will be understood that one or more components of the manual force/torque vector can be represented by a negative value, e.g., force components that are in a direction away from the planned trajectory T or in a direction away from the virtual force/torque vector.

The summation in block 111 results in a determination by the processor of an input force/torque vector that is applied to the robotic arm actuators 17 via admittance control (block 115). Admittance control is a feedback control algorithm implemented by the processor in the control tower 3 to guide the arm 4/docking interface 27. It receives, as input the summation produced in block 111 and based on feedback from force/torque sensors in the arm 4 issues velocity commands to the robotic arm actuators 17 to drive one or more portions (such as joints or links) of the robotic arm 4. The velocity commands may contain compensation as computed by the admittance control algorithm, and are updated as the arm/docking interface is driven toward alignment with and moving along the planned trajectory T. In one variation, the signals provided to the robotic arm actuators 17 by the processor under admittance control can include force or torque commands. The aforementioned admittance control of the robotic arm 4 via processor-controlled activation of the robotic arm actuators 17 (including blocks 103-111) can be performed as an iterative process, e.g., such that the input virtual force/torque vector and the manual force/torque vector summed by the processor to effect admittance control of the robotic arm can be updated repeatedly, e.g., at predetermined intervals, to provide updated signals to drive the robotic arm actuators 17 that reflect changes of the input force/torque vectors over time.

There is another mode of operation in which the robotic arm 4 moves only due to operator-forced manual guidance—essentially no movement of the robotic arm 4 is affected by the robotic arm actuators 17 along the planned trajectory (and under processor control). This mode may be an alternative to any of the admittance control modes (in lieu of block 115), and may be selected by an operator at any point during the docking process, as desired by the operator. For instance, the operator may wish to deviate from the planned trajectory T or would like the automatic guidance to be stopped for some reason, changing to an operator-only force or fully manual mode of operation. Switching between admittance control and fully manual control of the robotic arm 4 can be triggered or selected by a button 75 (e.g., see FIG. 6) located on or near the docking interface 27. The button 75 may actuate a switch (not shown) that is in electronic communication with the processor. The button 75 is used to generically refer to any suitable manual control interface that is selectable by an operator's hand or foot to for example toggle between the two modes. It may for example be a foot pedal located at the platform 5 (see FIG. 1). The button 75 when pressed or otherwise selected can signal the processor in the control tower 3 to stop admittance control driving of the robotic arm actuators 17 and instead enter another mode of operation in which the operator's manual force alone is allowed to move the robotic arm 4, even deviating from the planned trajectory. In that mode, the robotic arm 4 is said to be guided by the operator, deviating if desired from the planned trajectory T. Note however that even in this fully manual mode of operation, the processor may need to drive the actuators 17 to perform active gravity compensation and active back-driving (to overcome gravity and gear train friction at the various joints of the arm 4 so that the arm 4 moves smoothly and responsive to the operator's hand, yet remains stationary when not being forced by the operator). In another variation, the button 75 can be a mechanical or electromechanical control that directly disengages or deactivates the robotic arm actuators 17.

During fully manual guidance of the robotic arm 4, feedback on the positioning of the robotic arm 4/docking interface 27 relative to the planned trajectory T can be provided to an operator. Such feedback may, for example, be in the form of an audible beep or audible alarm (e.g., whenever the arm 4 deviates from the planned trajectory T), an indicator light or other visual indicia (e.g., glows green so long as the arm remains on the planned trajectory T), a graphical indicator being shown on a display next to the platform 5 or on the user display 15 at the user console 2, a tactile indicator such as haptic or vibratory feedback on a portion of the robotic arm 4, or other suitable technique for giving the operator feedback on how the manual guidance is progressing.

Figure 11:
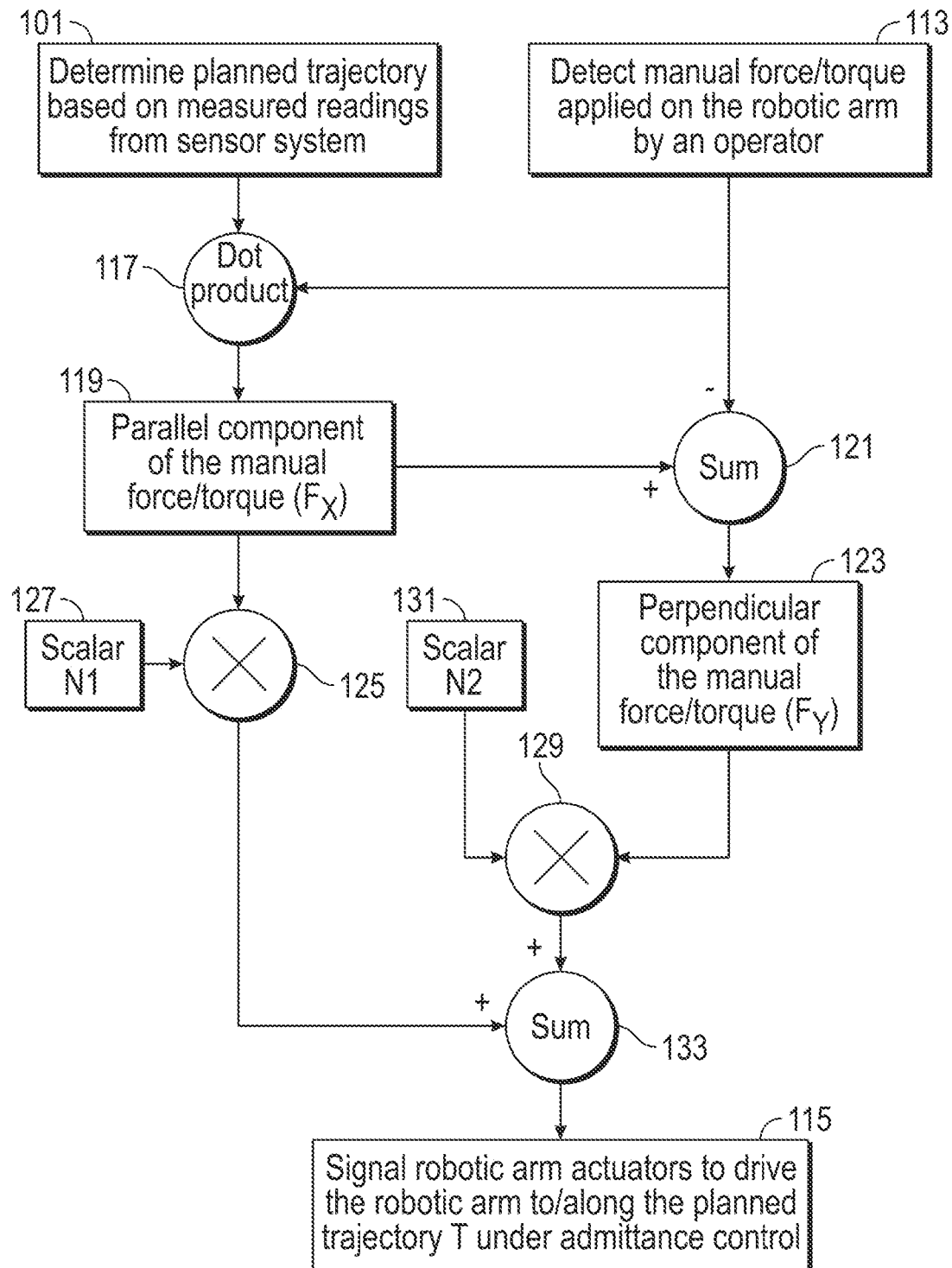
FIG. 11 is a process flow of a process flow for a method for docking a tool drive attached to a robotic arm of a surgical robotic system to a trocar according to one aspect of the disclosure.

Turning now to FIG. 11, a process flow of a passive virtual fixture mode of operation is shown, in which the processor constrains the robotic arm 4 to the planned trajectory T and only drives the arm 4 forward along the planned trajectory T if it detects that the operator is applying manual force to the arm 4 (in the direction of the planned trajectory T). At block 101, the planned trajectory T is generated by the processor in response to signals received from the sensor system 47, or by manual input, as described above. At block 113, the manual force/torque vector applied on the robotic arm 4 by an operator is detected by the processor from signals received from the F/T sensor 73 as described above, and, at block 117, the dot product of the planned trajectory T and the manual force/torque vector is calculated by the processor to determine a component of the manual force/torque vector provided by the operator that is parallel to or otherwise along the planned trajectory T at block 119 (hereafter, "$F_X$"). At block 121, the component of the manual force/torque vector $F_X$ along the planned trajectory T is subtracted from the total manual force/torque vector applied on the robotic arm 4 by the operator as measured by the F/T sensor 73 to provide a component of the manual force/torque vector that is perpendicular to the planned trajectory T at block 123 (hereafter, "$F_Y$").

Thereafter, at block 125, the processor multiplies the parallel component of the manual force/torque vector $F_X$ by a scalar value, e.g., a scalar value greater than 1 (hereafter, "scalar value N1", illustrated at block 127), such that this parallel manual force/torque vector component $F_X$ is amplified or otherwise increased in value. At block 129, the perpendicular component of the manual force/torque vector $F_Y$ is also multiplied by a scalar value, e.g., a scalar value less than 1 (hereafter, "N2", illustrated at block 131), such that this perpendicular manual force/torque vector component $F_Y$ is attenuated or otherwise decreased in value.

It will be understood that the scalar values N1, N2 can be related to the spring constant (k) that are modeled or generated by the processor as described above, and can be predetermined values or inputs that are determined by the processor or can be manually provided by an operator. In one variation, N2 is less than one (reduce or scale down) while N1 is greater than one (increase or scale up). This means that it will feel "easy" for the operator to force the arm 4 along the trajectory T, but the operator will feel resistance when pulling or pushing the arm 4 in a direction away from the trajectory T. In another variation, one or both of the scalar values N1, N2 can be a value of 1 such that the value of a respective manual force/torque vector component $F_X$, $F_Y$ determined by the processor is unmodified by the processor.

At block 133, the force/torque vector components $F_X$, $F_Y$ that have been multiplied by the respective scalar values N1, N2 are summed by the processor to generate signals to the robotic arm actuators 17 that effect admittance control of the robotic arm 4 by the robotic arm actuators 17 under control of the processor at block 115, as described above.

In this regard, robotic arm actuators 17 under control of the processor can assist manual guidance of the robotic arm 4 by the operator along the planned trajectory T, e.g., through modulation of the vector components of a manual force/torque vector applied to the robotic arm 4 by an operator relative to the planned trajectory T, so as to assist manual forcing of the robotic arm 4 by an operator along the planned trajectory T, and to resist manual forcing of the robotic arm 4 by an operator away from the planned trajectory T. In one variation, the scalar value N2 can be a value of zero such that the value of the force/torque vector component $F_Y$ is attenuated to a value of zero or canceled out, e.g., such that manual guidance of the robotic arm 4 away from the planned trajectory T by an operator is substantially inhibited or prevented by action of the robotic arm actuators 17 under control of the processor.

The admittance control of the robotic arm 4 via processor-controlled activation of the robotic arm actuators 17 in accordance with FIG. 11 can be performed as an iterative process, including the aforementioned modulation of the parallel component of the manual force/torque vector $F_X$ and the perpendicular component of the manual force/torque vector $F_Y$ via the respective scalar values N1, N2, to effect admittance control of the robotic arm 19. In this regard, the input to the admittance control (block 115) can be updated by repeatedly, e.g., at predetermined intervals, performing blocks 113-133 to provide updated signals to the robotic arm actuators 17 in response to changes of the input manual force/torque vectors over time.

Figure 12A:
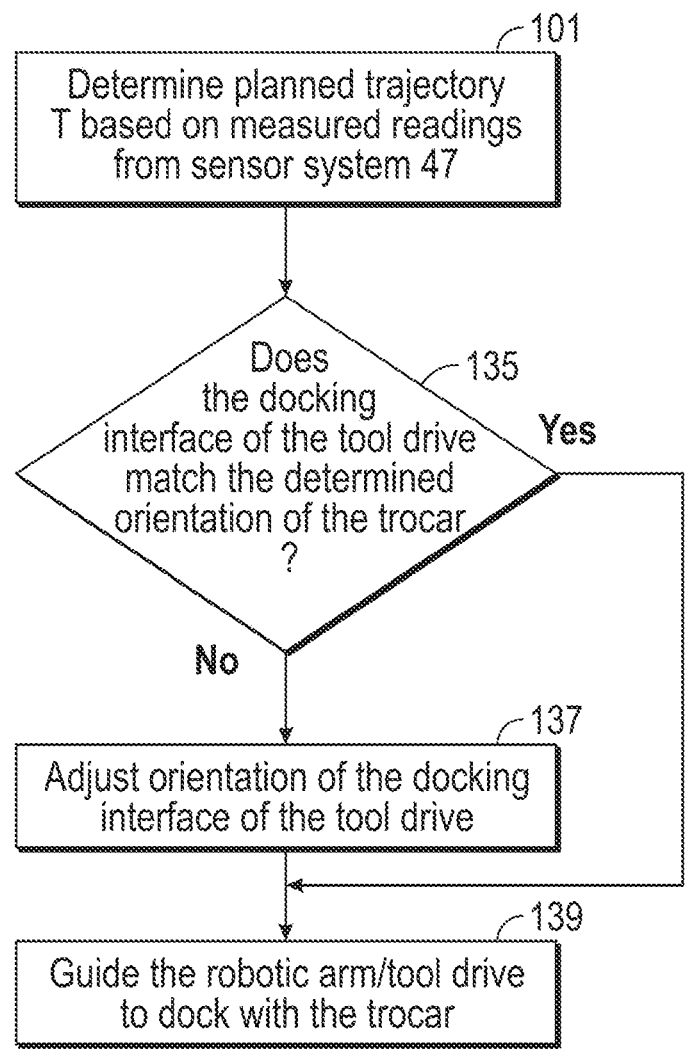
FIG. 12A is a process flow of a method for docking a tool drive attached to a robotic arm of a surgical robotic system to a trocar according to one aspect of the disclosure.

FIG. 12A illustrates a process flow of a method for docking a tool drive to a trocar, in the situation where during guidance or driving of the robotic arm 4 by the robotic arm actuators 17 (based on the planned trajectory T), the processor checks the pose of the docking interface 27, e.g., to confirm whether the orientation of the docking interface 27 matches an entry pose, i.e., the orientation and pose of the trocar 63 at which a mere linear translation movement will achieve docking (block 135). If the processor determines that the docking interface 27 does not match the determined orientation of the trocar 63, the processor can control the robotic arm actuators 17 to further drive or guide the robotic arm 4 toward such orientation (block 137). Once the orientation of the docking interface 27 matches the orientation of the trocar 63, the processor can drive the robotic arm actuators 17 to further drive or guide the robotic arm 4, e.g., only in a translation movement (no need to now change the pose or orientation of the docking interface 27), until the tool drive 23 docks with the trocar 63 (block 139). In such a process, the orientation of the docking interface 27 during the guidance along the planned trajectory T need not match that of the trocar 63 until reaching the entry pose.

Figure 12B:
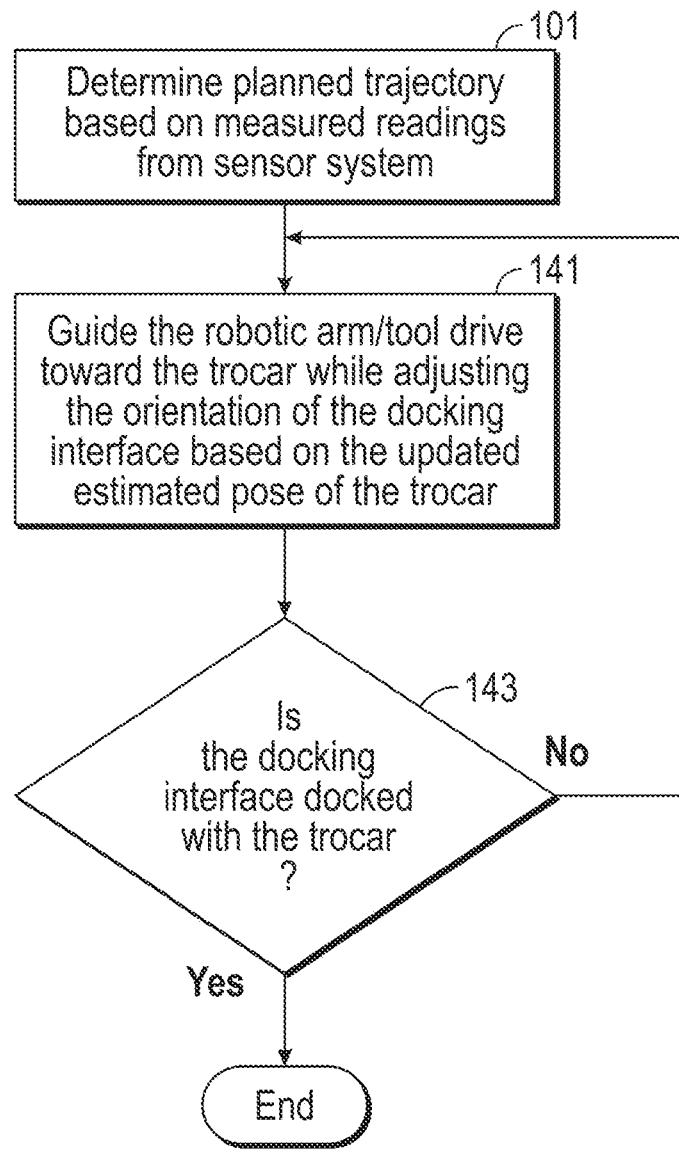
FIG. 12B is a process flow of a method for docking a tool drive attached to a robotic arm of a surgical robotic system to a trocar according to one aspect of the disclosure.

FIG. 12B shows another example process flow of a method for docking a tool drive that is attached to a robotic arm of a surgical robotic system, to a trocar. The process begins with having determined the planned trajectory T (block 101). The processor also determines a pose of the trocar 63, and then determines whether or not the current pose of the docking interface 27 matches that of the trocar 63 (e.g., an "entry pose" which is a pose of the docking interface 27 at which a linear translation of the docking interface 27 would be sufficient for to dock with the head of the trocar 63). If not, then processor adjusts the orientation of the docking interface (by appropriately driving the actuators 17 of the arm 4) so that the entry pose is matched. At that point, guidance of the arm along the planned trajectory T can start or resume (block 141). The processor can repeatedly, e.g., periodically, check the pose of the docking interface 27 while guiding the arm 4 (block 141), e.g., to confirm whether the docking interface 27 matches the entry pose, during the guidance. If not, then the processor determines how to adjust the orientation of the docking interface 27 and drives the actuators 17 in the arm 4 accordingly (block 141) while continuing to guide the arm along the planned trajectory T as described above. This continues until the docking interface has reached and matched the orientation of the head of the trocar 63, e.g., where the attachment portion 69 of the trocar 63 is at least partially surrounded or received in the receiving space 38 of the receiver 37 such that the docking interface 27 and the trocar 63 have the same pose, e.g., same position and orientation, i.e., within a tolerance (block 143). Once the orientation of the docking interface 27 and position thereof matches the orientation and position of the trocar 63, the processor can declare a docked state (and the process ends). In one variation, docked engagement of the docking interface 27 with the trocar 63 can be visually confirmed by an operator. If the docking interface 27 is determined by the processor to have docked with the trocar 63, the algorithm may be considered to be complete, and, in one variation, visual, audible, or tactile confirmation can be provided to an operator by the processor. If the docking interface 27 has been determined by the processor not to have docked with the trocar 63, the processor can signal the robotic arm actuators 17 to further guide or drive the robotic arm 4 until docking of the tool drive 23 with the trocar 63 is achieved.

Such guidance or driving of the robotic arm 19 into docking engagement with the trocar 63 can also be performed through the processor controlled assistance or resistance by the robotic arm actuators 17 of an operator's manual guidance of the robotic arm 19 according to a virtual spring as described above, or can be guided fully manually by an operator as described above.

In the docked pose, the docking interface 27 can be locked, e.g., rigidly mechanically coupled, with the trocar 63, for example, via the clamp components 33, 35, as described further below. In one variation, the state in which the attachment portion 69 of the trocar 63 is at least partially surrounded or received in the receiving space 38 of the receiver 37 can be considered as a ready to dock state, and the locked or mechanically coupled engagement of the docking interface 27 can be considered a docked or finally docked state.

Upon such positioning of the attachment portion 69 of the trocar 63 in the receiving space 38 of the receiver 37 of the docking interface 27, the lever 45 can be moved, e.g., manually or through an actuator under processor control, to a forward locked position to urge the clamp component 33 (FIG. 4) into pressable engagement with the attachment portion 69 of the trocar 63 such that the attachment portion 69 is secured, e.g., latched, clamped or locked, to the docking interface 27 in the docked position. Furthermore, the lever 45 can be moved rearward to the unlocked position to disengage the clamp component 33 from the attachment portion 69 to uncouple the robotic arm 19/docking interface 27 from the trocar 63.

When the trocar 63 is locked to the docking interface 27, one or more surgical tools can be coupled to the tool drive 23 and inserted through the trocar 63 to access a body cavity of the patient 6 (to perform subsequent surgical operations therein). The surgical robotic system 1 has the capability to uniquely identify each tool (endoscope and surgical instruments) as soon as it is attached and display the tool type and arm location, for example, on the display 15 at the user console 2. The corresponding tool functions are then enabled and can be activated using the UID 14 and the foot-operated controls 13. A patient-side assistant, e.g., the bedside operator 8, can attach and detach the tools, as required throughout the procedure. The surgeon (operator 9) seated at the user console 2 can begin to perform surgery using the tools that the operator 9 controls via manipulation of the UID 14 and the foot-operated controls 13. The system 1 translates the surgeon's hand, wrist, and finger movements through the UID 14 and the foot-operated controls 13 into precise real-time movements of the surgical tools.

The aforementioned arrangement of the sensor system 47 and the robotic arm 4 controlled algorithmically using inputs from at least the sensor system 47, and, optionally, a manual force/torque applied to the robotic arm 4 by the bedside operator 8, provide a smooth, at least partially processor-controlled guidance of the arm 4 to dock with the trocar 63. Once docked, a rigid or stable mechanical connection between the trocar 63 and the docking interface 27 of the robotic arm 4/tool drive 23 can be made, by a latching mechanism (for example under manual operator control).

In another aspect, when performing the docking process in either passive virtual fixture mode or active virtual fixture mode, the arm 4 could still move to a position or orientation which may cause loss of visual tracking. This may happen when, for example, the trocar 63 leaves the field of view of the imaging system of the arm, or another object obstructs the line of sight from the imaging sensor in the arm to the trocar 63, such that the control system may not have sufficient confidence that its planned trajectory T will lead to docking with the trocar. To avoid this loss of tracking issue, another layer of virtual fixtures can be used to keep the sensed surface feature of the trocar within the sensing range of the arm, throughout the motion of the arm along the planned trajectory. For instance, in the case of visual tracking of the trocar with a camera integrated on the arm as described above, the control system could generate a virtual spring between the sensed (tracked) surface feature on the trocar and the center of arm's sensing range (e.g., the middle of the camera's field of view as shown in FIG. 6). That virtual spring ensures that when following the planned trajectory, the tracked/sensed surface feature is maintained close to the center of the camera view. As a result, this prevents the sensed surface feature from leaving the sensing range of the imaging system, during motion of the robotic arm throughout docking process. The active/passive virtual fixtures described above for pulling or guiding the arm toward the trocar along the planned trajectory can be superimposed with this second virtual fixture. The latter will resist any motion of the arm that will cause the sensed surface feature to leave the arm imaging system's sensing range, thereby ensuring a more reliable and uninterrupted docking process.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, and they thereby enable others skilled in the art to best utilize the invention and various embodiments with various modifications as are suited to the particular use contemplated.

What is claimed is:

1. A surgical robotic system, comprising:
   a tool drive to be coupled to a distal end of a surgical robotic arm, the tool drive comprising a docking interface to receive a trocar and configured to secure an attachment portion of the trocar to the docking interface;
   one or more sensors operable to visually sense a surface feature of the trocar as image data; and
   one or more processors configured to
      determine a position of the trocar,
      generate a planned trajectory that includes a pre-determined path generated independently of the image data, wherein the planned trajectory starts from a known pose of the docking interface to the determined position of the trocar and is generated based on i) a log of prior movements of the surgical robotic arm and ii) signals received from a plurality of force or torque sensors in the surgical robotic arm, and
      signal a plurality of actuators in the arm to guide the robotic arm so that the tool drive, coupled to the distal end of the arm, is guided toward the determined position of the trocar along the pre-determined path.

2. The surgical robotic system of claim 1, wherein the one or more processors are configured to guide the robotic arm by controlling the plurality of actuators to automatically drive the arm along the planned trajectory.

3. The surgical robotic system of claim 1, wherein the one or more processors are configured to guide the robotic arm by controlling the plurality of actuators to assist an operator who is manually forcing the arm.

4. The surgical robotic system of claim 1, wherein the one or more processors are configured to control the plurality of actuators to resist an operator's manual forcing of the robotic arm when the operator's manual forcing is directing the robotic arm away from the planned trajectory.

5. The surgical robotic system of claim 4, wherein the actuators controlled by the one or more processors resist an operator's manual guidance of the robotic arm away from the planned trajectory with a force that is proportional to a distance between the robotic arm and the planned trajectory.

6. The surgical robotic system of claim 1 wherein the planned trajectory avoids collision of the robotic arm with one or more of a patient, a table on which the patient rests, bedside staff, a cable, a pipe, and other surgical robotic arms.

7. The surgical robotic system of claim 1, wherein the arm comprises a switch that when manually actuated by an operator changes a mode of operation between a first mode in which the one or more processors guide the robotic arm under admittance control of the actuators, and a second mode in which the one or more processors control the actuators to enable fully manual guidance of the robotic arm.

8. The surgical robotic system of claim 1, wherein the trocar has been inserted into a body of a patient on a table, and the one or more processors determine the position of the trocar by computing a location of a head of the trocar using a physical model having knowledge of a type of surgery, a size of the patient, a location and an orientation of the patient on the table, and a location of the trocar as inserted into the patient.

9. A surgical robotic system comprising:
   a tool drive to be coupled to a distal end of a surgical robotic arm, the tool drive comprising a docking interface to receive a trocar and configured to secure an attachment portion of the trocar to the docking interface;
   one or more sensors operable to visually sense a surface feature of the trocar as image data; and
   one or more processors configured to
      determine a position of the trocar,
      a) generate a planned trajectory that includes a pre-determined path generated independently of the image data, wherein the planned trajectory starts from a first, known position of the docking interface to a second position of the docking interface, wherein the second position is closer to the determined position of the trocar than the first, known position, the planned trajectory computed by the one or more processors based on i) a log of prior movements of the arm and ii) signals received from a plurality of force or torque sensors in the arm, and
      b) guide the robotic arm along the planned trajectory.

10. The surgical robotic system of claim 9 wherein the one or more processors are configured to respond to the second position of the docking interface having been reached by providing an alert or feedback to an operator of the system, the system further comprising a switch that, when actuated, signals the processor to i) activate the one or more sensors, ii) determine the position of the trocar based on the visually sensed surface feature, or iii) guide the robotic arm toward the position of the trocar that is determined based on the visually sensed surface feature.

11. The surgical robotic system of claim 1, wherein the one or more sensors are disposed in the docking interface.

12. The surgical robotic system of claim 11, wherein the docking interface comprises a sterile adapter coupled to a frontal portion thereof, the one or more sensors being mounted on the sterile adapter.

13. A method for docking a robotic arm of a surgical robotic system to a trocar, the method comprising:
  determining, by one or more processors, a position of the trocar by computing a location of a head of the trocar using a physical model having knowledge of a type of surgery, a size of a patient on a table, a location and an orientation of the patient on the table, and a location of the trocar as inserted into the patient;
  calculating, by the one or more processors, a planned trajectory from a known pose of a docking interface on the robotic arm to the determined position of the trocar, wherein the planned trajectory is calculated based on i) a log of prior movements of the arm and ii) signals received from a plurality of force or torque sensors in the arm; and
  driving, by the one or more processors, a plurality of actuators in the robotic arm to guide the docking interface along the planned trajectory.

14. The method of claim 13, further comprising determining, by the one or more processors, a distance between the docking interface and the planned trajectory, and controlling the plurality of actuators in the robotic arm to guide the robotic arm toward the planned trajectory based on the distance.

15. The method of claim 13, further comprising determining, by the one or more processors, a component of a manual force applied by an operator on the robotic arm in the direction of the planned trajectory, and controlling the plurality of actuators in the robotic arm to guide the robotic arm along the planned trajectory based on the component of the manual force applied by the operator along the planned trajectory.

16. The method of claim 15, wherein the one or more processors control the plurality of actuators in the robotic arm to guide the robotic arm along the planned trajectory with a force determined by a product of i) the component of the manual force applied by the operator along the planned trajectory and ii) a predetermined scalar value.

17. The method of claim 13, further comprising determining, by the one or more processors, a component of a manual force applied by an operator on the robotic arm in a direction away from a direction of the planned trajectory, and controlling the plurality of actuators in the robotic arm to drive the robotic arm toward the planned trajectory based on the component of the manual force applied by the operator in the direction away from the planned trajectory.

18. The method of claim 17, wherein the one or more processors control the plurality of actuators in the robotic arm to drive the robotic arm toward the planned trajectory with a force determined by a product of i) the component of the manual force applied by the operator in the direction away from the planned trajectory and ii) a predetermined scalar value.

19. The method of claim 13, further comprising:
  producing, by one or more sensors operable to visually sense a surface feature of the trocar, an image of the surface feature of the trocar, wherein the one or more sensors are part of a camera on the arm, and the one or more processors control the plurality of actuators in the robotic arm to maintain the surface feature at a center of a field of view of the camera while the arm moves along the planned trajectory.

* * * * *